(12) United States Patent
Fehr

(10) Patent No.: US 9,834,818 B2
(45) Date of Patent: Dec. 5, 2017

(54) METHOD OF QUANTITATING THE AMOUNT OF A TARGET NUCLEIC ACID IN A SAMPLE

(71) Applicant: Siemens Healthcare Diagnostics Inc., Tarrytown, NY (US)

(72) Inventor: Adrian Nielsen Fehr, San Francisco, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 428 days.

(21) Appl. No.: 14/439,677

(22) PCT Filed: Oct. 23, 2013

(86) PCT No.: PCT/US2013/066294
§ 371 (c)(1),
(2) Date: Apr. 30, 2015

(87) PCT Pub. No.: WO2014/070540
PCT Pub. Date: May 8, 2014

(65) Prior Publication Data
US 2015/0275291 A1  Oct. 1, 2015

Related U.S. Application Data

(60) Provisional application No. 61/721,151, filed on Nov. 1, 2012.

(51) Int. Cl.
*C12P 19/34* (2006.01)
*C12Q 1/68* (2006.01)

(52) U.S. Cl.
CPC ......... *C12Q 1/6874* (2013.01); *C12Q 1/6851* (2013.01)

(58) Field of Classification Search
USPC ....................... 435/6.12, 91.1, 91.2
See application file for complete search history.

(56) References Cited

U.S. PATENT DOCUMENTS

| | | |
|---|---|---|
| 2003/0124521 A1 | 7/2003 | Coull et al. |
| 2003/0143527 A1 | 7/2003 | Shyamala |
| 2004/0091905 A1* | 5/2004 | Guo ............... C12Q 1/6858 435/6.12 |
| 2009/0068645 A1 | 3/2009 | Sibson |
| 2009/0186349 A1 | 7/2009 | Gunderson et al. |

OTHER PUBLICATIONS

Watanabe et al. "Use of a competitive probe in assay design for genotyping of the UGT1A1*28 microsatellite polymorphism by the smart amplification process", 43: 479-484, (2007).
International Search Report for PCT/US2013/066294 dated Jan. 29, 2014.

* cited by examiner

*Primary Examiner* — Kenneth Horlick

(57) ABSTRACT

The method includes obtaining a sample including a target nucleic acid, contacting the sample with a quantification primer, adding a quantity of blocking primer to the sample, and repeating the contacting and adding steps until the total quantity of blocking primer present in the sample meets or exceeds the amount of target present in the sample. Each repetition utilizes a quantification primer having a different unique identifying feature assigned to sequentially increasing quantification levels, and the quantity of blocking primer added at each repetition establishes numerical spacing between the quantification levels. The method further includes identifying the unique identifying feature present in any bound quantification primers that remain in the sample, where the presence of a unique identifying feature assigned to a particular quantification level indicates the approximate amount of the target present in the sample.

28 Claims, 11 Drawing Sheets

1. Add 100 copies of "$10^2$"

2. Add 1,000 copies of "block"
3. Add 100 copies of "$10^3$"

4. Add $10^4$ copies of "block"
5. Add 100 copies of "$10^4$"

6. Add $10^5$ copies of "block"
7. Add 100 copies of "$10^5$"

8. Add $10^6$ copies of "block"
9. Add 100 copies of "$10^6$"

10. Add $10^8$ copies of "block"
11. Add 100 copies of "$10^8$"

12. Add magnetic dT beads
 - Mix and pull down
 - Remove supernatant

13. To supernatant, add dA-antiHyb and dT beads
 - Mix and pull down
 - Remove supernatant 14. Transcribe/copy targets (optionally amplify)
- Add reverse transcriptase (RT)/DNA polymerase to transcribe/copy RNA/DNA targets 15. Complete platform – specific library prep and sequence

```
                             SEQUENCE LISTING

<160> NUMBER OF SEQ ID NOS: 11

<210> SEQ ID NO 1
    <211> LENGTH: 24
    <212> TYPE: DNA
    <213> ORGANISM: Artificial Sequence
    <220> FEATURE:
    <223> OTHER INFORMATION: Hybridization Domain

<400> SEQUENCE: 1
agagaaagag cagaagacag tggc                                               24

<210> SEQ ID NO 2
    <211> LENGTH: 29
    <212> TYPE: DNA
    <213> ORGANISM: Artificial Sequence
    <220> FEATURE:
    <223> OTHER INFORMATION: Hybridization Domain

<400> SEQUENCE: 2
ccttgtaagt cattggtctt aaaggtacc                                          29

<210> SEQ ID NO 3
    <211> LENGTH: 30
    <212> TYPE: DNA
    <213> ORGANISM: Artificial Sequence
    <220> FEATURE:
    <223> OTHER INFORMATION: Quantification Primer

<400> SEQUENCE: 3
atcacgagag aaagagcaga agacagtggc                                         30

<210> SEQ ID NO 4
    <211> LENGTH: 30
    <212> TYPE: DNA
    <213> ORGANISM: Artificial Sequence
    <220> FEATURE:
    <223> OTHER INFORMATION: Quantification Primer

<400> SEQUENCE: 4
cgatgtagag aaagagcaga agacagtggc                                         30

<210> SEQ ID NO 5
    <211> LENGTH: 30
    <212> TYPE: DNA
    <213> ORGANISM: Artificial Sequence
    <220> FEATURE:
```

```
<223> OTHER INFORMATION: Quantification Primer

<400> SEQUENCE: 5
ttaggcagag aaagagcaga agacagtggc                                  30

<210> SEQ ID NO 6
<211> LENGTH: 30
<212> TYPE: DNA
<213> ORGANISM: Artificial Sequence
<220> FEATURE:
<223> OTHER INFORMATION: Quantification Primer

<400> SEQUENCE: 6
tgaccaagag aaagagcaga agacagtggc                                  30

<210> SEQ ID NO 7
<211> LENGTH: 30
<212> TYPE: DNA
<213> ORGANISM: Artificial Sequence
<220> FEATURE:
<223> OTHER INFORMATION: Quantification Primer

<400> SEQUENCE: 7
tgaccaagag aaagagcaga agacagtggc                                  30

<210> SEQ ID NO 8
<211> LENGTH: 30
<212> TYPE: DNA
<213> ORGANISM: Artificial Sequence
<220> FEATURE:
<223> OTHER INFORMATION: Quantification Primer

<400> SEQUENCE: 8
gccaatagag aaagagcaga agacagtggc                                  30

<210> SEQ ID NO 9
<211> LENGTH: 29
<212> TYPE: DNA
<213> ORGANISM: Artificial Sequence
<220> FEATURE:
<223> OTHER INFORMATION: Quantification Primer

<400> SEQUENCE: 9
cagatcagag aaagagcaga agacagtgg                                   29

<210> SEQ ID NO 10
<211> LENGTH: 44
<212> TYPE: DNA
<213> ORGANISM: Artificial Sequence
<220> FEATURE:
<223> OTHER INFORMATION: Blocking primer

<400> SEQUENCE: 10
aaaaaaaaaa aaaaaaaaaa agagaaagag cagaagacag tggc                  44

<210> SEQ ID NO 11
<211> LENGTH: 44
<212> TYPE: DNA
<213> ORGANISM: Artificial Sequence
<220> FEATURE:
<223> OTHER INFORMATION: Anti-hybridization Primer

<400> SEQUENCE: 11
aaaaaaaaaa aaaaaaaaaa tctctttctc gtcttctgtc accg                  44
```

METHOD OF QUANTITATING THE AMOUNT OF A TARGET NUCLEIC ACID IN A SAMPLE

This application incorporates by reference the sequence listing which is submitted together with this application in computer readable form which has the file name 2012P18661WOUSSequenceList_ST25.txt and is 3 KB.

BACKGROUND

According to the World Health Organization, 33.3 million people worldwide were living with Human Immunodeficiency Virus ("HIV") as of 2009. That same year, 2.6 million new infections were reported and 1.8 million people worldwide died of AIDS-related illnesses.

Human immunodeficiency virus type 1 (HIV-1) enters host cells through a multistep process that requires sequential interactions of the envelope glycoprotein gp120. The envelope protein interacts first with the CD4 receptor and then with one of a family of chemokine coreceptors, mainly CCR5 or CXCR4. The V3 loop in HIV-1 gp120 has been shown to be critical for coreceptor binding.

Importantly, HIV-1 strains can be phenotypically classified according to a virus' ability to use the CCR5 (R5) and/or CXCR4 (X4) co-receptor. Pure R5-tropic and pure X4-tropic virus can use only the CCR5 and CXCR4 co-receptors to enter the target cell, respectively, while dual-tropic virus can use both co-receptors. In a virus population, the use of both co-receptors can be due either to the presence of dual-tropic clones or to a mixture of pure R5-tropic and X4-tropic clones or both. This is cumulatively defined as dual/mixed phenotype.

HIV-1 co-receptor usage is of central pathological and clinical importance. It has been shown that R5-tropic viruses are generally responsible for the establishment of the initial infection and predominate in the majority of newly HIV-1 infected patients, while the use of the CXCR4 co-receptor is generally seen in more advanced stages of disease, and has been associated with a more rapid CD4 decline and progression to AIDS.

HIV-1 co-receptor usage is also of critical therapeutic importance given the current and future approval of CCR5 antagonists for the treatment of HIV-1 infection. CCR5-antagonists are a new class of anti-HIV-1 drugs that specifically inhibit the entry of R5-tropic HIV-1 strains into the target cells by allosteric inhibition of the CCR5 co-receptor. Maraviroc is the first approved CCR5 antagonist, which entered clinical practice in 2007.

Significantly, HIV-1 tropism must be determined before CCR5 antagonists can be prescribed. CCR5-antagonists are most effective (and the viruses less likely to develop resistance) when administered to treatment-naïve patients. This is due to the higher prevalence of CCR5-tropic HIV-1 early in the infection cycle and relative to more advanced patients. Moreover, CCR5 antagonists are ineffective against X4-tropic viruses.

The mandatory determination of HIV-1 tropism prior to administration of CCR5 antagonists presents several practical difficulties. A number of phenotypic assays have been developed, such as the Trofile® assay (Monogram Biosciences). Trofile® is a single-cycle recombinant virus assay in which a pseudovirus is generated from full length envelope (env) genes derived from the patient's virus population. The complete envelope is used to determine viral tropism taking into account determinants that lie outside the V3 loop. However, phenotypic assays are complex and marked by high cost and long turnaround times. In addition, most of them cannot determine HIV-1 tropism in clinical samples with viral loads below 1,000 copies/ml and have an unacceptably high sensitivity threshold for detection of the minority X4-tropic virus population. Thus, a need exists for genotypic tropism assays that can rapidly and efficiently determine tropism based on the sequence of a patient-derived V3 loop in HIV-1 gp120.

In addition to these genotyping needs, there is a long-felt need for accurate quantification of HIV-1 RNA and proviral DNA. RNA quantification, also referred to as viral load measurements, are routinely used in clinical settings. (FIG. 1). Indeed, studies have shown HIV-1 RNA levels to be a predictor of the time to progression to acquired immunodeficiency syndrome (AIDS) and death that is independent of CD4 cell counts. Viral load measurements are also useful in determining when to initiate anti-retroviral therapy and in monitoring the response to such therapy. In specific situations, HIV-1 RNA and proviral DNA levels may also be useful in diagnosing of HIV infection. For example, serologic testing may not reliably identify HIV-1 infection in neonates with passively acquired maternal HIV-1 antibodies or with incompletely developed immune systems, in individuals with early infection (<30 days from infection), or with "indeterminate" antibody profiles by Western blot assays. In these situations, detection and quantification of HIV-1 nucleic acids (RNA or proviral DNA) can provide early evidence of HIV-1 infection (approximately 10-14 days after infection) and can also provide early evaluation of the progression of infection.

SUMMARY

Besides the HIV-1 examples described above, there are many diagnostic applications that require or can be improved by providing both quantitative information and sequence identity. Currently, two separate techniques are commonly required to address these needs; for example, quantitative PCR ("qPCR") to count the copy number of a given target (e.g., original infectious particles) and capillary electrophoresis sequencing for genotyping. Although tremendous advances have been made in the throughput and accuracy of genotyping thanks to next-generation sequencing ("NGS") systems, similar advances have not been realized for quantification.

One challenge for quantification with NGS is that most samples to be genotyped require end-point amplification such that input quantity is lost. Another challenge is that the dynamic range of sequencing instruments used as "genomic counters" is limited by the maximum number of reads per run (up to approximately millions of reads on bench top systems). However, measurements of less than 100 reads are strongly impacted by counting statistics, such that the effective minimum dynamic ranges is only about $10^4$. There is also a direct tradeoff between dynamic range for quantification (i.e., being able to count targets present in a range from very few to very many) and the quality of genotyping at low input levels, which is generally very poor.

Disclosed herein are methods, compositions, systems and kits that can simultaneously provide sequence identity and quantification of nucleic acid targets. These embodiments result from the discovery that quantitative information can be encoded or embedded into a target sequence, read-out during sequencing-based genotyping and associated with a defined quantification level. With regard to NGS systems, the quantitative information can be encoded/embedded before end-point amplification. Thus, the embodiments disclosed herein provide the synergistic benefits of combining heretofore separate modalities (quantification and sequencing) into a single procedure. These embodiments can be applied to increase throughput and accuracy, as well as minimize labor and cost, relative to current separate sequencing/quantification systems. Embodiments of the invention can also be cost-effectively multiplexed in order to further increase throughput.

The embodiments described herein generally comprise obtaining a sample comprising a target nucleic acid and contacting the sample with a quantification primer. The quantification primer comprises a hybridization domain complementary to a region of the target and is of sufficient length to hybridize specifically with the target under reasonable conditions. It is generally present in an amount less than or equal to the amount of target present in the sample, and comprises a unique identifying feature assigned to a first quantification level. In other embodiments, the amount of quantification primers exceeds the total number of copies of the target present in the sample. After the quantification primers assigned to a first quantification level are added to the sample, an amount of blocking primer is added to the sample. The blocking primer is typically added in an amount in excess of the amount of the preceding quantification primer, although in some embodiments the amount may be less than amount of the preceding quantification primer. Moreover, the blocking primer can bind at least part of the region of the target that is complementary to the quantification primer, thereby blocking the region from contact with the quantification primer. Thus, the blocking primer binds a portion of the amount of the target in the sample not bound by quantification primer, thereby blocking said portion from contact with any subsequent quantification primer comprising the same target-specific hybridization domain. The blocking primers do not need to contain the entire target-specific hybridization domain of the quantification primers as long as the blocking primer is able to bind or overlap the same binding region of the target as the quantification primer to such an extent that subsequent quantification primers cannot bind copies of the target to which the blocking primers are bound. The cycle of adding quantification primers assigned to a particular quantification level followed by addition of blocking primer is repeated until the total quantity of blocking primer present in the sample meets or exceeds the amount of target. In general, each repetition utilizes a different quantification primer comprising the same or substantially the same (i.e., capable of hybridizing to the same binding region of the target) hybridization domain but possessing a different unique identifying feature assigned to sequentially increasing quantification levels. In some embodiments, substantially the same amount of quantification primer will be added at each repetition. In some embodiments, the quantity of blocking primer added at each repetition establishes numerical spacing (i.e., granularity or resolution) between the quantification levels. By analogy, the quantification primers and their associated levels are like the rungs of a ladder, while the amount of blocking primers added between subsequent quantification primers establishes the distance between the rungs.

The needs of given assay or application to which embodiments of the invention are applied dictate the number of quantification levels and the amount of blocking primer added at each repetition. For example, considering applications drawn to HIV infection, upper limits beyond 10,000,000 copies per milliliter of patient plasma lack clinical relevance and, therefore, are not needed.

After a sufficient amount of quantification primers and blocking primers have been added for the maximal desired detectable quantity, any target bound by the blocking primers, unbound blocking primers and unbound quantification primers are removed from the sample in most embodiments. Quantification primers and the target copies bound by the quantification primers can then be identified via the identifying features present in the quantification primers. In some embodiments, the identifying feature is a probe or beacon that emits a signal specific for a particular quantification level. In other words, the quantification primers are identified by emission of a signal, with each quantification primer emitting a discrete signal specific to the quantification level to which it has been assigned. In some embodiments, the identifying feature is a nucleotide sequence (i.e., the quantification primers comprise a "a unique identifying sequence") and quantification primers and/or targets to which they are bound are identified by sequencing. In preferred embodiments, at least the quantification primers are sequenced to identify the quantification levels with which the primers are associated. In some embodiments, only the quantification primers are sequenced. For example, a unique identifying sequence may also correspond with a target-specific sequence of interest (e.g., polymorphism) that is sufficient for a particular assay. In some embodiments, at least a portion of the target is sequenced. In some embodiments, at least a portion of both the quantification primers and the target are sequenced. In some embodiments, the unique identifying features are embedded or incorporated into the target. In some embodiments, binding of the quantification primers to copies of the targets is itself sufficient to embed quantifying information into the targets. In other embodiments, quantifying information is embedded by enzymatic manipulations (e.g., amplification) of the quantification primer:target pairs, thereby producing a template into which the unique identifying has been incorporated. In some embodiments, the entire template is subsequently sequenced. In other embodiments, only a portion of the template is sequenced. At the least the unique identifying sequence present in the quantification primer and incorporated into the template is sequenced in most embodiments. In some embodiments, at least a portion of the unique identifying sequence incorporated into the template is sequenced, thereby indicating the presence of a polymorphism present in the target. Regardless of the means of identification, the presence of a unique identifying feature corresponding to a particular quantification level indicates the approximate amount of target present in the sample.

In some embodiments, the targets comprise nucleic acid sequences. In some embodiments, the nucleic acid is DNA. In other embodiments, the nucleic acid is RNA. In some embodiments, the targets comprise members of a DNA library. In some embodiments, the targets comprise nucleic acids derived directly from a subject or sample obtained from a subject, wherein the presence and amount of one or nucleic acid targets provides diagnostic information on the presence or absence and severity of a disease or medical condition.

In some embodiments, the quantification primers are oligonucleotides. In some embodiments, the quantification primers comprise deoxyribonucleotides. In some embodiments, the quantification primers hybridize to a complementary single-stranded sequence within a target. In some embodiments, the quantification primers are at least partially single-stranded. In some embodiments, the quantification primers are subsequently incorporated into the target through PCR amplification or reverse transcription. In some embodiments, the quantification primers are approximately 10-75 base pairs in length. In particular embodiments, the quantification primers are about 35 base pairs in length. In some embodiments, the quantification primers further comprise base modifications. In some embodiments, the quantification primers in each repetition are identical except for the unique identifying sequence.

In some embodiments, the blocking primers are oligonucleotides. In some embodiments, the blocking primer oligonucleotides comprise a sequence substantially identical to the hybridization domain of the quantification primers and complementary to at least a portion of the same sequence within the binding region of the target. In some embodiments, both the quantification primers and the blocking primers are DNA. In some embodiments, the same amount of blocking primer is added at each repetition.

As described above, in some embodiments of the invention the methods further comprise sequencing the target. In some embodiments, the target is a polynucleotides. In some embodiments, the target is DNA. In other embodiments, the target is RNA. In some embodiments, the target is sequenced as avsingle-molecule template. In some embodiments, sequencing is done by a sequencing platform selected from Roche 454 platform, Illumina Genomic Analyzer, SOLID system, or Helicos True Single Molecule DNA sequencing.

In some embodiments of the invention, the steps of the methods are performed sequentially. In some embodiments, the steps are performed iteratively.

Further disclosed herein are kits comprising sets of target-specific quantification primers and blocking primers as described herein.

In some embodiment, the numerical spacing between quantification levels is on a logarithmic ("log") scale. In other embodiments, the numerical spacing increases linearly. In certain embodiments, the numerical spacing increases linearly by a factor of at least 50. In certain embodiments, the numerical spacing increases linearly by a factor of at least 100. In some embodiments, the numerical spacing increases linearly by a factor of approximately 1000.

In some embodiments of the invention, the methods are automated. In some embodiments, the target nucleic acids are viral RNA. In particular embodiments, the target nucleic acids are retroviral RNA. In some embodiments, the target nucleic acids are prokaryotic DNA. In certain embodiments, the target nucleic acids are of bacterial origin.

In some embodiments, the blocking primers further comprise an isolation feature that facilitates removal of unbound blocking primers and targets bound by the blocking primers. In some embodiments, the isolation feature is a nucleotide sequence. In some embodiments, unbound blocking primers and targets bound by the blocking primers are removed by hybridization of the isolation sequence with a solid substrate. In certain embodiments, the solid substrate is an antibody, magnetic bead, particle, polymeric bead, chromatographic resin, filter paper, membrane or hydrogel. In particular embodiments, the isolation sequence is a poly-adenosine tract. In some embodiments, the solid substrate is a magnetic bead comprising oligonucleotides with a poly-thymine sequence.

In some embodiments, unbound quantification primers are removed by adding an anti-hybridization primer comprising (1) a sequence complementary to the hybridization domain of the quantification primer, and (2) an isolation sequence. In some embodiments, the isolation sequence is a poly-adenosine tract. In some embodiments, a solid substrate is added comprising a sequence complementary to the isolation sequence, which facilitates removal of unbound quantification primers once bound or hybridized to the solid substrate. In certain embodiments, the solid substrate is an antibody, magnetic bead, particle, polymeric bead, chromatographic resin, filter paper, membrane or hydrogel. In particular embodiments, the solid substrate is a magnetic bead comprising oligonucleotides with a poly-thymidine sequence.

DEFINITIONS

Figure 1:
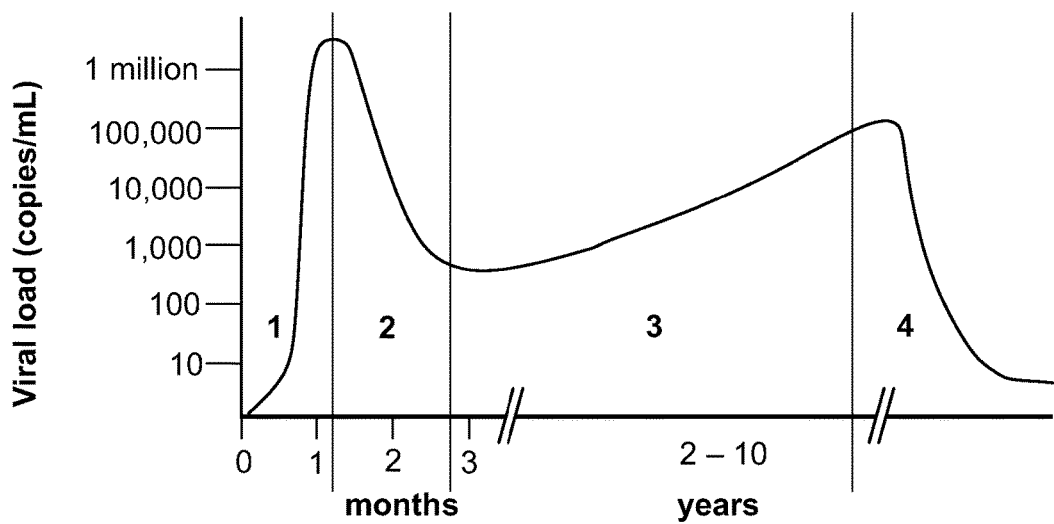
FIG. 1 is a time course graph of HIV viral loads as infection progresses. (1) A few weeks after infection, HIV viral load increases to very high levels. The can be millions of copies per ml, and makes the subject extremely infectious. (2) As the immune system fights back, viral load usually drops to lower levels. (3) Over 2-10 years, viral load increases. It is usually between 50,000-100,000 when HIV treatment is started. (4) Treatment should reduce viral load to less than 50 copies per ml within 3 months. All body fluids become dramatically less infectious.

The term "amplification" or "amplification reaction" is used herein to refer to any in vitro process for exponentially increasing the number of copies of a nucleotide sequence or sequences. Nucleic acid amplification results in the incorporation of nucleotides (ribonucleotides or deoxyribonucleotides) into primers to form DNA or RNA molecules that are complementary to a template nucleic acid molecule. As used herein, one amplification reaction may consist of many rounds of primer extension. For example, one PCR reaction may consist of several cycles of denaturation and extension ranging from, e.g., about 5 cycles to about 1000 cycles, or more.

The term "amplification reaction reagents", is used herein to refer to reagents used in nucleic acid amplification reactions and may include, but are not limited to, buffers, enzymes having reverse transcriptase and/or polymerase activity or exonuclease activity, enzyme cofactors such as magnesium or manganese, salts, nicotinamide adenine dinuclease (NAD) and deoxynucleoside triphosphates (dNTPs), such as deoxyadenosine triphosphate, deoxyguanosine triphosphate, deoxycytidine triphosphate and deoxythymidine triphosphate.

The term "gene", as used herein, has its art understood meaning, and refers to a part of the genome specifying a macromolecular product, be it DNA for incorporation into a host genome, a functional RNA molecule or a protein, and may include regulatory sequences (e.g., promoters, enhancers, etc.) and/or intron sequences preceding (5' non-coding sequences) and following (3' non-coding sequences) the coding sequences. Genes that are sequenced and quantitated in embodiments of the invention can be of any origin, including eukaryotic, prokaryotic, viral, microbial, mammalian, etc.

The term "hybridization", as used herein, refers to the formation of complexes (also called duplexes or hybrids) between nucleotide sequences which are sufficiently complementary to form complexes via Watson-Crick base pairing or non-canonical base pairing. It will be appreciated that hybridizing sequences need not have perfect complementary to provide stable hybrids. In many situations, stable hybrids will form where fewer than about 10% of the bases are mismatches. Accordingly, as used herein, the term "complementary" refers to a nucleic acid molecule that forms a stable duplex with its complement under particular conditions, generally where there is about 90% or greater homology (e.g., about 95% or greater, about 98% or greater, or about 99% or greater homology). Those skilled in the art understand how to estimate and adjust the stringency of hybridization conditions such that sequences that have at least a desired level of complementarity will stably hybridize, while those having lower complementarity will not. For examples of hybridization conditions and parameters, see, for example, Sambrook et al., "*Molecular Cloning: A Laboratory Manual*", 1989, Second Edition, Cold Spring Harbor Press: Plainview, N.Y. and Ausubel, "*Current Protocols in Molecular Biology*", 1994, John Wiley & Sons: Secaucus, N.J. Complementarity between two nucleic acid molecules is said to be "complete", "total" or "perfect" if all the nucleic acid's bases are matched, and is said to be "partial" otherwise.

The terms "labeled" and "labeled with a detectable agent (or moiety)" are used herein interchangeably to specify that an entity (e.g., quantification primer) can be visualized, e.g., directly or following hybridization to another entity that comprises a detectable agent or moiety. Preferably, the detectable agent or moiety is selected such that it generates a signal which can be measured and whose intensity is related to (e.g., proportional to) the amount of the entity of interest (e.g., a target sequence). Also preferably, quantification primers assigned to a particular quantification level may be labeled with the same detectable agent, while quantification primers assigned to other quantification levels may be respectively labeled with different detectable agents. Thus, in such embodiments, each quantification level will generate its own specific signal. Methods for labeling nucleic acid molecules are well-known in the art. In some embodiments, labeled nucleic acids can be prepared by incorporation of, or conjugation to, a label that is directly or indirectly detectable by spectroscopic, photochemical, biochemical, immunological, electrical, optical, or chemical means.

The term "nucleoside" as used herein, refers to adenine ("A"), guanine ("G"), cytosine ("C"), uracil ("U"), thymine ("T") and analogs thereof linked to a carbohydrate, for example D-ribose (in RNA) or 2'-deoxy-D-ribose (in DNA), through an N-glycosidic bond between the anomeric carbon of the carbohydrate (1'-carbon atom of the carbohydrate) and the nucleobase. When the nucleobase is purine, e.g., A or G, the ribose sugar is generally attached to the N9-position of the heterocyclic ring of the purine. When the nucleobase is pyrimidine, e.g., C, T or U, the sugar is generally attached to the N1-position of the heterocyclic ring. The carbohydrate may be substituted or unsubstituted. Substituted ribose sugars include, but are not limited to, those in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Ribose examples include ribose, 2'-deoxyribose, 2',3'-dideoxyribose, 2'-haloribose, 2'-fluororibose, 2'-chlororibose, and 2'-alkylribose, e.g., 2'-O-methyl, 4'-alpha-anomeric nucleotides, 1'-alpha-anomeric nucleotides (Asseline et al., Nucl. Acids Res., 19:4067-74 [1991]), 2'-4'- and 3'-4'-linked and other "locked" or "LNA," bicyclic sugar modifications (WO 98/22489; WO 98/39352; WO 99/14226).

The term "nucleotide" as used herein means a nucleoside in a phosphorylated form (a phosphate ester of a nucleoside), as a monomer unit or within a polynucleotide polymer. "Nucleotide 5'-triphosphate" refers to a nucleotide with a triphosphate ester group at the 5' position, sometimes denoted as "NTP", or "dNTP" and "ddNTP" to particularly point out the structural features of the ribose sugar. The triphosphate ester group may include sulfur substitutions for the various oxygen moieties, e.g., alpha-thio-nucleotide 5'-triphosphates. Nucleotides can exist in the mono-, di-, or tri-phosphorylated forms. The carbon atoms of the ribose present in nucleotides are designated with a prime character (') to distinguish them from the backbone numbering in the bases. For a review of polynucleotide and nucleic acid chemistry see Shabarova, Z. and Bogdanov, A. Advanced Organic Chemistry of Nucleic Acids, VCH, New York, 1994.

The terms "nucleic acid", "nucleic acid molecule", "polynucleotide" or "oligonucleotide" are used herein interchangeably. They refer to polymers of nucleotide monomers or analogs thereof, such as deoxyribonucleic acid (DNA) and ribonucleic acid (RNA). The nucleotides may be genomic, synthetic or semi-synthetic in origin. Unless otherwise stated, the terms encompass nucleic acid-like structures with synthetic backbones, as well as amplification products. As will be appreciated by one skilled in the art, the length of these polymers (i.e., the number of nucleotides it contains) can vary widely, often depending on their intended function or use. Polynucleotides can be linear, branched linear, or circular molecules. Polynucleotides also have associated counter ions, such as $H^+$, $NH_4^+$, trialkylammonium, $Mg^+$, $Na^+$ and the like. A polynucleotide may be composed entirely of deoxyribonucleotides, entirely of ribonucleotides, or chimeric mixtures thereof. Polynucleotides may be composed of internucleotide nucleobase and sugar analogs.

In some embodiments, the term "oligonucleotide" is used herein to denote a polynucleotide that comprises between about 5 and about 150 nucleotides, e.g., between about 10 and about 100 nucleotides, between about 15 and about 75 nucleotides, or between about 15 and about 50 nucleotides. Throughout the specification, whenever an oligonucleotide is represented by a sequence of letters (chosen, for example, from the four base letters: A, C, G, and T, which denote adenosine, cytidine, guanosine, and thymidine, respectively), the nucleotides are presented in the 5' to 3' order from the left to the right. A "polynucleotide sequence" refers to the sequence of nucleotide monomers along the polymer. Unless denoted otherwise, whenever a polynucleotide sequence is represented, it will be understood that the nucleotides are in 5' to 3' orientation from left to right.

Nucleic acids, polynucleotides and oligonucleotides may be comprised of standard nucleotide bases or substituted with nucleotide isoform analogs, including, but not limited to iso-C and iso-G bases, which may hybridize more or less permissibly than standard bases, and which will preferentially hybridize with complementary isoform analog bases. Many such isoform bases are described, for example, by Benner et al., (1987) Cold Spring Harb. Symp. Quant. Biol. 52, 53-63. Analogs of naturally occurring nucleotide monomers include, for example, 7-deazaadenine, 7-deazaguanine, 7-deaza-8-azaguanine, 7-deaza-8-azaadenine, inosine, nebularine, nitropyrrole (Bergstrom, J. Amer. Chem. Soc., 117: 1201-1209 [1995]), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990, 303), 2-azapurine (Seela, WO 01/16149), 2-thiopyrimidine, 6-thioguanine, 4-thiothymine, 4-thiouracil, 0-6-methylguanine, N-6-methyladenine, O-4-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127,121; Gall, WO 01/38584), and ethenoadenine (Fasman (1989) in Practical Handbook of Biochemistry and Molecular Biology, pp. 385-394, CRC Press, Boca Raton, Fla.).

The term "3" refers to a region or position in a polynucleotide or oligonucleotide 3' (i.e., downstream) from another region or position in the same polynucleotide or oligonucleotide. The term "5'" refers to a region or position in a polynucleotide or oligonucleotide 5' (i.e., upstream) from another region or position in the same polynucleotide or oligonucleotide. The terms "3' end" and "3' terminus", as used herein in reference to a nucleic acid molecule, refer to the end of the nucleic acid which contains a free hydroxyl group attached to the 3' carbon of the terminal pentose sugar. The term "5' end" and "5' terminus", as used herein in reference to a nucleic acid molecule, refers to the end of the nucleic acid molecule which contains a free hydroxyl or phosphate group attached to the 5' carbon of the terminal pentose sugar. In some embodiments of the invention, oligonucleotide primers comprise tracts of poly-adenosine at their 5' termini.

The term "isolated", as used herein, means a target, sample, polynucleotide, nucleic acid or oligonucleotide, which by virtue of its origin or manipulation, is separated from at least some of the components with which it is naturally associated or with which it is associated when initially obtained. By "isolated", it is alternatively or additionally meant that the target, sample, polynucleotide, nucleic acid or oligonucleotide of interest is produced or synthesized by the hand of man.

The term "primer", as used herein, typically refers to oligonucleotides that hybridize in a sequence specific manner to a complementary nucleic acid molecule (e.g., a target nucleic acid molecule comprising a sequence complementary to the hybridization domain present in a quantification primer and blocking primer). In some embodiments, a primer will comprise a region of nucleotide sequence (i.e., "hybridization domain") that hybridizes to (i.e., is complementary to) at least about 8, e.g., at least about 10, at least about 15, or about 20 to about 40 consecutive nucleotides of a target nucleic acid (i.e., will hybridize to a contiguous sequence of the target nucleic acid). In general, a primer sequence is identified as being either "complementary" (i.e., complementary to the coding or sense strand (+)), or "reverse complementary" (i.e., complementary to the antisense strand (−)). In some embodiments, the term "primer" may refer to an oligonucleotide that acts as a point of initiation of a template-directed synthesis using methods such as PCR (polymerase chain reaction) or reverse transcription under appropriate conditions (e.g., in the presence of four different nucleotide triphosphates and a polymerization agent, such as DNA polymerase, RNA polymerase or reverse-transcriptase, etc., in an appropriate buffer solution containing any necessary reagents and at suitable temperature(s)). Such a template directed synthesis is also called "primer extension". For example, a primer pair may be designed to amplify a region (e.g., the V3 region of the HIV env genomic sequence or a portion thereof) of cDNA or DNA using PCR. Such a pair will include a "forward primer" and a "reverse primer" that hybridize to complementary strands of a DNA molecule and that delimit a region to be synthesized and/or amplified.

The term "quantification level", as used herein, refers to an approximate threshold numerical quantity or amount of a target that may be present in a sample. Quantification levels are discrete units and can be designated or set at whatever level is necessary for a particular assay. For example, a first quantification level may be set at a numerical quantity of 50, 100, 1000, 10,000, 100,000, 1,000,000, etc. The numerical spacing between a first quantification level and the next highest quantification level may be alternatively referred to as "granularity" or "resolution". Numerical spacing is set by the amount of blocking primer added between addition of quantification primers associated with a first quantification level and addition of the next round of quantification primers associated with a sequentially higher quantification level. As mentioned, quantification levels are discrete designations. Thus, target quantity can be established to one or more quantification levels and be absent from other quantification levels. For example, after application of the embodiments disclosed herein, DNA sequencing can establish the presence of target copies with embedded identifying sequences corresponding to quantification levels of at least 1,000, 10,000, and 100,000 but not 1,000,000. Thus, the presence of a unique identifying sequence corresponding to a highest quantification level of 100,000 but not a quantification level of 1,000,000 indicates that there are between 100,000 to 1,000,000 copies of the target.

The term "quantification primer", as used herein, refers to a molecule capable of being attached to a target of interest. For example, in some embodiments of the invention, quantification primers comprising DNA or RNA are hybridized to a target-of-interest. In some embodiments, the quantification primers are at least partially single-stranded. In some embodiments, quantification primers comprise at least two domains: a first domain comprising an identifying feature unique to and corresponding with a particular quantification level; and a second binding domain capable of binding to a target. In some embodiments, the identifying feature is a nucleotide sequence, and the binding domain is a nucleotide sequence comprising a hybridization domain. In some embodiments, the identifying feature is a detectable probe, agent or moiety. In some embodiments, the identifying feature unique to a quantification level and the hybridization domain may comprise all or part of the same nucleotide sequence (i.e., a single nucleotide sequence that can serve as both a unique identifier and that can stably hybridize with a corresponding target sequence under suitable reaction conditions). The presence of a unique identifying feature allows the primer, or target into which the primer has been incorporated, to be established, correlated or associated with a particular quantification level. The unique identifying feature may alternatively be referred to as "zip codes" or "barcodes". In other words, the presence of a unique identifying feature or barcode within a quantification primer allows the approximate quantification of targets to which the primers are bound.

As used herein, the term "sample" refers to a biological sample obtained or derived from a source of interest, as described herein. In some embodiments, a source of interest comprises an organism, such as an animal or human. In some embodiments, a sample comprises nucleic acids or a set of nucleic acids (e.g., library) representing all or substantially of the nucleic acid sequences found in a source. In some embodiments, a biological sample or source of the sample comprises biological tissue or fluid. In some embodiments, a biological sample or source of the sample may be or comprise bone marrow, blood, blood cells, ascites, tissue or fine needle biopsy samples, cell-containing body fluids, free floating nucleic acids, sputum, saliva, urine, cerebrospinal fluid, peritoneal fluid, pleural fluid, feces, lymph, gynecological fluids, skin swabs, vaginal swabs, oral swabs, nasal swabs, washings or lavages such as a ductal lavages or broncheoalveolar lavages, aspirates, scrapings, bone marrow specimens, tissue biopsy specimens, surgical specimens, feces, other body fluids, secretions, and/or excretions, and/or cells therefrom, etc. In some embodiments, a biological sample or source of the sample is or comprises cells obtained from an individual. In some embodiments, a sample comprises plasma RNA and/or whole-blood DNA from a subject. In some embodiments, obtained cells are or include cells from an individual from whom the sample is obtained. In some embodiments, obtained cells are or include microbial cells of an individual's microbiome. In some embodiments, a sample or source is a "primary sample" if it is obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces, etc.), etc. In some embodiments, as will be clear from context, the term "sample" refers to a preparation that is obtained by processing (e.g., by removing one or more components of and/or by adding one or more agents to) a primary sample or source. For example, a "secondary sample" or "processed sample" may comprise nucleic acids or proteins extracted from a "primary sample" or obtained by subjecting a "primary sample" to techniques such as amplification or reverse transcription of mRNA, isolation and/or purification of certain components, etc.

As used herein, the terms "sequence determination", "determining a nucleotide sequence", "sequencing", and like terms, in reference to polynucleotides includes determination of partial as well as full sequence information of the polynucleotide. That is, the term includes sequence comparisons, fingerprinting, polymorphism identification and like levels of information about a target polynucleotide, as well as the express identification and ordering of each nucleoside of the target polynucleotide within a region of interest. In various embodiments "sequence determination" comprises identifying a single nucleotide, while in various embodiments more than one nucleotide is identified. Identification of nucleosides, nucleotides, and/or bases are considered equivalent herein. It is noted that performing sequence determination on a polynucleotide typically yields equivalent information regarding the sequence of a perfectly complementary (100% complementary) polynucleotide and thus is equivalent to sequence determination performed directly on a perfectly complementary polynucleotide.

The methods disclosed herein are not limited to or by particular sequencing platforms. Nonetheless, exemplary sequencing reactions include those based on techniques developed by Maxam and Gilbert, *Proc. Natl. Acad Sci USA*, 74:560, 1977 or Sanger, *Proc. Nat. Acad. Sci* 74:5463, 1977. It is also contemplated that any of a variety of automated sequencing procedures may be utilized when performing subject assays (*Biotechniques* 19:448, 1995, Venter et al., *Science,* 291:1304-1351, 2001, Lander et al., *Nature,* 409: 860-921, 2001), including sequencing by mass spectrometry (see, for example, U.S. Pat. No. 5,547,835 and international patent application Publication Number WO 94/16101, entitled DNA Sequencing by Mass Spectrometry by H. Koster, U.S. Pat. No. 5,547,835 and international patent application Publication Number WO 94/21822 entitled "DNA Sequencing by Mass Spectrometry Via Exonuclease Degradation" by H. Koster), and U.S. Pat. No. 5,605,798 and International Patent Application No. PCT/US96/03651 entitled DNA Diagnostics Based on Mass Spectrometry by H. Koster, Cohen et al. (1996) *Adv. Chromatogr.* 36:127-162, and Griffin et al. (1993) *Appl. Biochem. Biotechnol.* 38:147-159). It will be evident to one skilled in the art that, for certain embodiments, occurrence of only one, two or three nucleic acid bases need be determined in a sequencing reaction (e.g., identification of a particular polymorphism or viral strain). Yet other sequencing methods are disclosed, e.g., in U.S. Pat. No. 5,580,732 entitled "Method of DNA sequencing employing a mixed DNA-polymer chain probe", U.S. Pat. No. 5,571,676 entitled "Method for mismatch-directed in vitro DNA sequencing", and U.S. pre-grant publication 2010/0092960 entitled "Helicase-assisted sequencing with molecular beacons." Exemplary NGS techniques for use in embodiments of the invention include those described in Metzker, M. L., *Nature Review Genetics,* 2010, 11:31-46, and Shendure J. and Hanlee, J., *Nat. Biotech.,* 2008, 26:1135-1145.

The term "target" is used herein to refer to any specimen-, nucleic acid- or polynucleotide-of-interest in a sample (e.g., viral RNA) that is desired or selected to be quantified and sequenced through the methods disclosed herein. The target may be a gene, a regulatory sequence, genomic DNA, environmental DNA, cDNA, mRNA or any portion of the foregoing. Targets may be directly or indirectly derived from any cell or virus, whether living or dead. Targets may be directly or indirectly derived from any sample, including human clinical samples (including whole blood, plasma, cancer cells, tumor cells, etc.), bacterial cells, viruses, fungi, protists, parasites and other pathogens. In preferred embodiments of the invention, targets are or are rendered at least partially single-stranded.

In some embodiments of the invention, at least a portion of both the target and the quantification and blocking primers will be single-stranded. In other embodiments, however, only one or the other is single-stranded.

The term "tropism" is used herein to refer to the affinity of a viral particle (such as HIV) for particular cell and receptor types (such as CCR5 or CXCR4). "Tropic variant" is used herein to refer to HIV genomic sequence variations associated with a tropism.

DETAILED DESCRIPTION OF SOME EMBODIMENTS

Figure 2:
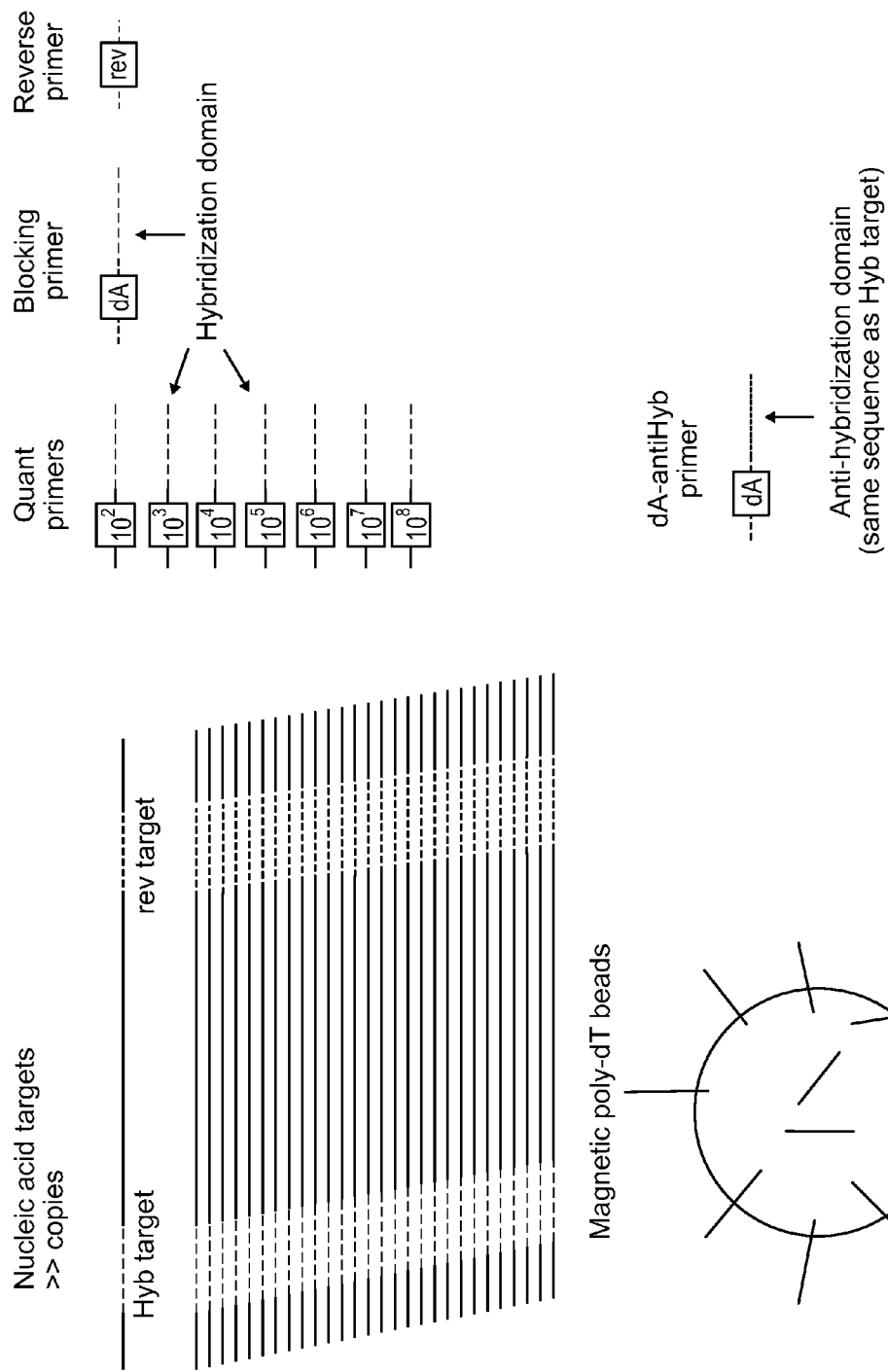
FIG. 2 is representation of standard components of some embodiments of the invention.

Embodiments of the invention are based on a principle of encoding or "barcoding" quantification information into a target nucleic acid. Constituent elements of some embodiments of the invention are depicted in FIG. 2: nucleic acid targets present in a plurality of copies and comprising a hybridization target region and a region to which a reverse primer can bind for optional PCR amplification; oligonucleotide quantification and blocking primers comprising hybridization domains that can bind to the hybridization target region; optionally reverse primers for PCR amplification; anti-hybridization ("anti-hyb") primers that comprise a sequence corresponding to at least part of the hybridization target region and that can bind unbound quantification primers; and solid supports for isolation of unbound blocking primers, blocking primers bound to target copies, and bound or unbound anti-hyb primers.

In general, groups of quantification primers are designed such that each group comprises a hybridization domain specific for a target and a unique identifying feature (e.g., nucleotide sequence) assigned by a user to a particular quantification level. Thus, the quantification primer groups can be stratified to increasing levels of quantification, although the choice of which identifying sequence to assign to a particular quantification level and the numerical spacing (i.e., granularity) between the quantification levels are completely at the user's discretion. In other words, a counting regime can be designed and tailored to a specific need or application (e.g., a particular diagnostic test). Each group of quantification primers will typically comprise the same hybridization domain but have a different unique identifying feature (e.g., nucleotide sequence), thus ensuring that each group is associated with only one quantification level.

In some embodiments, quantification primers may be described as "bifunctional". For example, one portion (i.e., the hybridization domain) serves to hybridize to free copies of the target through complementary base pairing. Another portion, which in some embodiments can partially or completely overlap the hybridization domain, contains a unique identifying sequence or "barcode" that designates it as belonging to a particular quantification level and distinguishes it from all other quantification levels. In other words, each unique barcode corresponds to a specific quantification level (i.e., 1000 level, 10,000 level, etc.). In some embodiments, the quantification primers are approximately 10-75 base pairs in length. In some embodiments, at least a portion of the quantification primers is single-stranded, which facilitates interaction with single-stranded areas of the target. In some embodiments, quantification primers comprise components in addition to oligonucleotides (e.g., polypeptides, sugars, polymers, fatty acids, etc.). In certain embodiments, the quantification primers are labeled with fluorophores and optionally molecules capable of quenching fluorescence when in close proximity to the fluorophores.

In some embodiments of the invention, quantitative information can be embedded into quantification primers via attachment of a detectable agent (e.g., moiety, probe or beacon) that is specific for a particular quantification level. In other words, the detectable agent produces a signal that can be detected and converted into quantitative information. In some embodiments, the detectable agent is a fluorophore. In some embodiments, the detectable agent is a combination of fluorophore and a quenching molecule that quenches fluorescence of the fluorophore when in close proximity. In some embodiments of the invention, the fluorophore is in close proximity to the quencher when the quantification primers are bound to a target. A primer-displacing enzyme (e.g., DNA helicase, RNA helicase, RNA/DNA helicase, DNA polymerase, reverse transcriptase or the like) or an enzyme with nuclease activity can be applied during pre-sequencing processing (e.g., amplification), which removes the fluorophore or otherwise separates the fluorophore from a quencher, thereby allowing the fluorophore to produce an optical signal. Each set of quantification primers associated with a particular quantification level can be correlated with a specific detectable agent capable of producing a discrete detectable signal. The discrete signals can be detected during pre-sequencing processing. A signal belonging to a given group of primers indicates that the target is present in at least an amount corresponding to the quantification level associated with that particular signal. In other words, the unique identifying signal corresponding to the highest quantification (and the corresponding absence of signal associated with any higher quantification levels) reflects the approximate original input level. Methods adaptable to embodiments of the invention are known in the art and have been described previously, including U.S. pre-grant publication No. 2010/0092960 and U.S. Pat. No. 5,538,848 herein incorporated by reference.

After a group of primers corresponding to a particular quantification level is added to a sample to contact the target, blocking primers are added to the sample. Blocking primers generally comprise part or all of same hybridization domain as the quantification primers. Thus, blocking primers are able to hybridize to free copies of target and prevent further interaction with any further added quantification primers specific for that sequence of the target. After blocking primers are added, quantification primers corresponding with the next quantification level can be added. Thus, the amount of blocking primer added between additions of quantification primers establishes the numerical spacing (i.e., granularity) between the quantification levels assigned to particular groups of quantification primers.

An important feature of the blocking primer is that they must comprise some feature to facilitate their isolation (and, correspondingly, copies of the target to which they are bound). In some embodiments, the isolation feature is a nucleic acid sequence. In some embodiment, this sequence is a poly-adenosine ("polyA") tract—i.e., a polyA tail. In other embodiments, this sequence is any string of nucleotides that is not a polyA tail, is not substantially complementary to any sequence of the target greater than five, ten or fifteen nucleotides, and is different from the unique identifying sequence of the quantification primers. The tails (polyA or otherwise) can be located 3', 5' or anywhere within the blocking primers. In some embodiments, the blocking primers are approximately 10-50 base pairs in length. In some embodiments, at least a portion of the blocking primers is single stranded, which facilitates interaction with single-stranded areas of the target.

Figure 3:
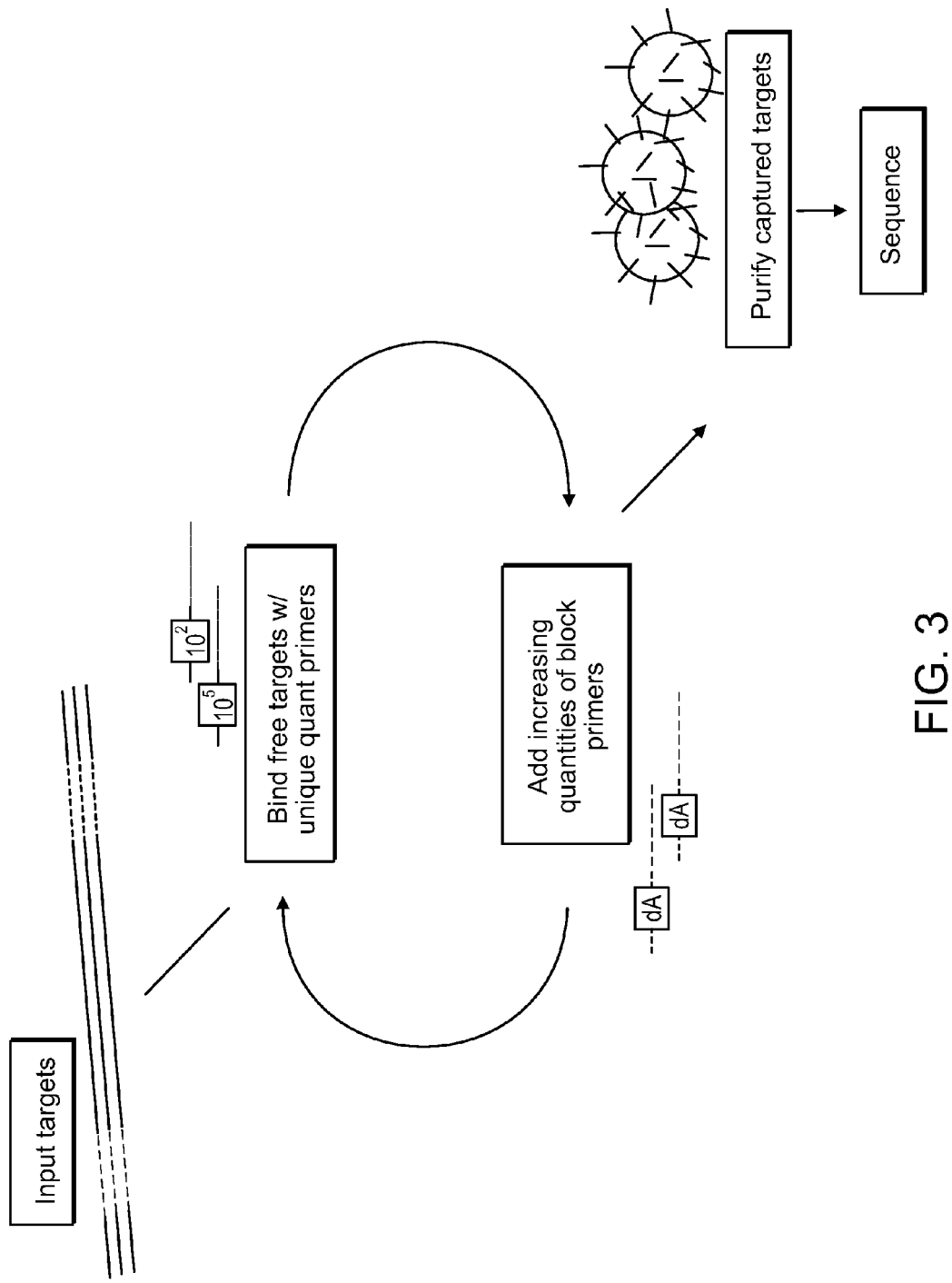
FIG. 3 is a general flow diagram of some embodiments of the invention.

As the quantification primer groups are sequentially contacted with copies of the target, each group associated with a particular quantification level is able to bind copies of the target until (1) all of the primers of a given group are bound to a target copy, or (2) all of the target copies are bound by one primer group or another or by the blocking primers; i.e., the target copies are saturated. In other words, the steps of (1) adding quantification primer associated with a particular quantification level, followed by (2) adding blocking primer that can compete with the quantification primers for binding to the target, can be repeated or cycled until the desired dynamic range is covered (i.e., the amount of blocking primer meets or exceeds the desired, e.g., clinically relevant, or expected target maximum). (FIG. 3). At the saturation point, primers associated with increasingly higher quantification levels are unable to bind copies of the target. Because the quantifying primer groups are stratified and sequentially contacted with the target copies, the binding of at least one primer belonging to a given group indicates that the target is present in at least an amount corresponding to the quantification level associated with that particular group. In other words, the unique identifying feature corresponding to the maximal target quantity reflects the approximate original input level. Correspondingly, the absence of primers associated with the next highest quantification level indicates that the target is present in an amount less the quantification level associated with that particular group. Likewise, the absence of primers corresponding to the lowest quantification level indicates that the target is present, if at all, in an amount less than that quantification level (e.g., less than 50 copies, less than 100 copies, etc.). Thus, embodiments of the invention are able to quantify the target within a precise level that is customizable to the needs and discretion of a given user or application.

Three key parameters impact applications of embodiments of the invention; these parameters can be customized or manipulated based on the resolution required for a particular application. The first is the amount of quantification primers added at each step. In some embodiments of the invention, about 50, 100, 200, 300, 400, 500, 600, 700, 800, 900, 1000 or more copies of quantification primers can be added at one step or all the steps of a given application. The second parameter is the dynamic range over which it is desired to detect target inputs. The lower limit is set by the number of quantification primers used per cycle or step (as described above). The upper limit is set by the maximal desirable detectable quantity, and can be practically any number. In other words, the sequence/cycle of quantification primers followed by blocking primers (with the quantification level increasing at each step) can be repeated as necessary until a maximal desirable detectable quantity is reached. The third parameter is the numerical spacing or granularity within the dynamic range. As mentioned, the numerical spacing between quantification levels is largely determined by the amount of blocking primer added between a first quantification level and the next quantification level. For example, if 100 copies of quantification level 1 primers are added at step 1, followed by X amount of blocking primers, then 100 copies of quantification level 2 primers are added at step 2, quantification level 2 will correspond to an approximate level of 100+X+100. X can be any number.

In some embodiments, the amount of blocking primer added at each step is selected for linear granularity; i.e., the same amount of blocking primer is added at each step or cycle. In some embodiments, about 100, 200, 300, 400, 500, 600, 700, 800, 900, 1000, 2000, 3000, 4000, 5000, etc. copies of blocking primers can be added at each step. For example, if 1000 copies of blocking primer are added at each step, then the quantification levels will be set in sequentially increasing increments of 1000; e.g., there will be about 1000, 2000, 3000, 4000, 5000, etc. copies of the target present. Linear embodiments provide low dynamic range but higher resolution. In some embodiments of the invention, the amount of blocking primer added at each step is selected for logarithmic granularity. For example, if 10 times more blocking primer is added at each step, then the quantification levels will be logarithmic, increasing at spaced increments corresponding to 1, 10, 100, 1000, etc. (instead of 1, 2, 3, 4, etc. as in a linear scale). In some embodiments, the quantification levels increase logarithmically in a manner corresponding to 1000, 10,000, 100,000, 1,000,000 or 10,000,000 copies of the target. Embodiments of the invention are amenable to any logarithmic scale. Embodiments with logarithmic granularity offer increased dynamic range but lower resolution. In some embodiments of the invention, linear spacing may be used over a one range of target amount and logarithmic spacing applied over a second range.

Ultimately, the combined choice of the three parameters can be determined by the balance of desired lower/upper detection limits, workflow complexity tolerance (although the entire process is easily automatable), test duration requirements, and stability of quantification primer/target interaction, among other considerations. It is well within the capabilities of one of ordinary skill in the art to set, balance and evaluate the parameters for a particular assay or embodiment. Those of skill in the art will also appreciate that many different patterns of variegation can be developed and applied to customize the quantification schemes. For example, in some embodiments, various blocking steps can be optionally omitted such that labeling with two different quantification primers occurs sequentially. More specifically, there can be two sequential additions of quantification primers with 50 copies of quantification level 1 primers and 50 copies of quantification level 2 primers. This can be followed by addition of 900 copies of blocking primers. The measurement then delivers quantitative information corresponding to target copy numbers below 50, 50-100 copies and greater than 1000 copies.

Importantly, some embodiments of the invention are able to embed the quantification information into the target copies until such time as the identifying sequence can be ascertained. In some embodiments, quantifying information is captured in the targets via enzymatic manipulation that uses the bound quantification primers to catalyze the reaction. The embedded quantifying information can then be carried along until nucleic acid sequencing reveals the identity of unique identifying sequence, which then indicates that the target is present at least in an amount corresponding to that quantification level. (FIG. 3).

However, in this embodiment, in order for the quantifying information to actually reflect the amount of target present, unbound quantification primers, unbound blocking primers and copies of the target bound by blocking primers must first be removed from the system. (FIG. 3). Removal of free blocking primers and copies of the target bound by blocking primers is facilitated by the isolation feature of the blocking primers described above. These features allow the blocking primers (and anything bound to it) to be removed, for example, by interaction with a complementary feature affixed to a solid support. In some embodiments, the interaction is hybridization with a complementary nucleic acid sequence. For example, a polyA tail can hybridize to a polyT sequence. In some embodiments, the interaction may involve an antibody that binds to the isolation feature.

Removal of unbound quantification primer is facilitated by the addition of anti-hyb primers that comprise at least part of the hybridization target region ("anti-hybridization domain") to which the hybridization domain of the quantification primers can bind. Thus, after the point at which there are no longer free copies of the target capable of binding the quantification primers, the hybridization domain of the quantification primers is free to interact with the "anti-hybridization domain" of the anti-hyb primers. Anti-hyb primers will also bind any residual unbound blocking primers comprising a sequence complementary to the anti-hyb domain. The anti-hyb primers comprise an isolation feature similar to that of the blocking primers described above, which allows the anti-hyb primers, and any primers to which they are bound, to be isolated by interaction with a complementary feature affixed to a solid support. In some embodiments, the interaction is hybridization with a complementary nucleic acid sequence. For example, a polyA tail can hybridize to a poly-thymine ("polyT") tract. In some embodiments, the interaction may be an antibody that binds to the isolation feature of the anti-hyb primers. In some embodiments, the isolation feature of the anti-hyb primers is different than the isolation feature of the blocking primers.

The invention is not limited by the solid support, or "substrate" or "phase" with which the blocking primers and anti-hyb primers interact. A "solid support", as used herein, refers to any material that is insoluble, or can be made insoluble by a subsequent reaction. In some embodiments, the solid supports are coated or bound to an entity that directly interacts with the isolation features of the blocking and anti-hyb primers (e.g., a polyT tract that can interact with a polyA tail). In other embodiments, the solid supports themselves directly interact with the isolation features. Examples of commonly used solid phase materials include, but are not limited to, glass or polymeric tubes which are coated with an antibody on their internal surfaces, coated polymeric inserts, coated polymeric sticks, micro and macro beads formed of polymers and of glass, magnetic beads or particles, porous matrices, coated membranes, tablets, latex particles, microparticles, membranes, plastic tubes, walls of microtiter wells, glass or silicon chips, a chromotagraphic resin, filter paper, and hydrogel.

Nucleic Acid Targets

Embodiments of the invention are directed to the sequencing and quantification of nucleic acid targets. More specifically, embodiments of the invention can provide data on the absolute copy number of a specific target and provide the nucleic acid sequence of the target. In general, the embodiments disclosed herein entail hybridization of quantification primers and blocking primers to nucleic acid targets of interest that are at least partially single-stranded. In certain embodiments, this can include hybridizing the primers to one strand of a double-stranded nucleic acid that has been made single stranded by, e.g., denaturation, enzymatic digestion of one strand, or other available methods, e.g., those described in U.S. patent application Ser. No. 12/383,855 and U.S. patent application Ser. No. 12/286,119.

Embodiments of the invention are useful in any application requiring (or that be improved by) information on the quantity and identity of nucleic acid targets. Some embodiments of the invention can be applied to HIV nucleic acid sequences, in particular to quantification and sequencing of regions that encode the V3 region of the env glycoprotein for the determination of HIV tropism and severity of infection. In some embodiments the primers are used in nested PCR methods for the detection or sequencing of the V3 region of the env gene. Oligonucleotide primers for use in some embodiments of the invention are disclosed in U.S. provisional application 61/711,785, filed Oct. 10, 2012, incorporated herein by reference. Unique identifying feature can be integrated into these primers and assigned to specific quantification levels for use in the embodiments disclosed herein. Additional diseases for which embodiments of the invention may be particularly amenable include hepatitis C virus, hepatitis B virus, human papilloma virus, and cancer.

Applicable targets in embodiments of the invention can be derived from virtually any source. Typically, the targets comprise polynucleotides. Targets may be DNA, RNA or combinations thereof. Target nucleic acids may comprise additional molecules, such as proteins, carbohydrates, fluorophores, polymers, etc. Targets may be derived from viruses, microbes, eukaryotes, prokaryotes, or any type of cell. Targets may be derived from representative locations along a chromosome of interest, a chromosomal region of interest, an entire genome of interest, a cDNA library, RNA library, RNA isolated from subjects and the like. The targets may be of various sizes, from tens to thousands of bases long.

Targets may be obtained from samples. Samples can be obtained from a single source (e.g., one patient or tissue) or from multiple sources. Samples may be obtained from a plurality of subjects, tissues, etc. In some embodiments, samples are obtained from a single subject at multiple time points and the differences between the time points ascertained.

The amount of target present in a sample can vary dramatically depending on the amount the sample, sample amount, etc. In some embodiments of the invention, target amount is represented on a per target basis. That is, the absolute number (e.g., copy number) of a target can be on the order of approximately 10,000,000, 1,000,000, 100,000, 10,000, 1000, 900, 800, 700, 600, 500, 400, 300, 200, 100, 90, 80, 70, 60, 50, 40, 30, 20, 10, 5 or fewer copies. In some embodiments of the invention, target amount may be defined by mass. For example, the amount of a particular target may be on the order of approximate 50 µg, 25 µg, 10 µg, 5 µg, 1 µg, 500 ηg, 100 ηg, 90 ηg, 80 ηg, 70 ηg, 60 ηg, 50 ηg, 40 ηg, 30 ηg, 20 ηg, 10 ηg, 5 ηg, 1 ηg, 500 picograms, etc.

Preparation of RNA

In some embodiments, the disclosed methods may involve some level of RNA preparation. The targets described above may themselves be RNA; for example, viral RNA isolated from a subject.

When an RNA preparation step is included in the disclosed embodiments, the method of RNA preparation can be any method of RNA preparation that produces enzymatically manipulatable RNA. For example, the RNA can be isolated by using the guanidinium isothiocyanate-ultracentrifugation method, the guanidinium and phenol-chloroform method, the lithium chloride-SDS-urea method or poly A+/mRNA from tissue lysates using oligo(dT) cellulose method, e.g., see Schildkraut et al., *J. Mol. Biol.* 4, 430-433 (1962); Chomczynski and Sacchi, *Anal. Biochem.* 162:156 (1987); Auffray and Rougeon, *Eur. J. Biochem.* 107:303-314 (1980); Aviv and Leder, *Proc. Natl. Acad. Sci. USA* 69, 1408-1412 (1972); and Sambrook et al., Selection of poly A+ RNA in "Molecular Cloning", Vol. 1, 7.26-7.29 (1989).

RNA can be isolated from any desired cell or cell type and from any organism, including mammals, such as mouse, rat, rabbit, dog, cat, monkey, and human, as well as other non-mammalian animals, such as fish or amphibians, as well as plants and even prokaryotes, such as bacteria. Thus, DNA or cDNA utilized in disclosed embodiments can also be from any organism, such as that disclosed for RNA.

Primers

In embodiments of the invention, copies of a given target are bound by quantification and blocking primers. In some embodiments of the invention, the quantification and blocking primers are site-specific; i.e., bind to a specific hybridization region within the target. In other embodiments, the primers are non-site-specific. In some embodiments, the primers bind a terminal region of the target. In some embodiments, terminal primers may be either at the 5' or 3' end of the target.

In some embodiments, quantification primers are bifunctional, comprising at least two domains: a first domain comprising a unique identifying feature (e.g., nucleotide sequence) assigned to a particular quantification level, and a second hybridization domain capable of hybridizing to a sequence within the target. The unique identifying feature allows for quantifying information to be embedded into target copies bound by the primers. Within a given application, each identifying feature must be unique for a specific quantification level and readily discernible from the identifying features associated with other quantification levels. And within a given application, the quantification primers will generally comprise the same or substantially similar hybridization domains such that the quantification primers in each cycle bind to the same region of the target.

The domains of the quantification primers may, but need not, overlap. In some embodiments, the identifying feature is a polynucleotide sequence, and the binding domain is a polynucleotide sequence comprising a hybridization domain. In some embodiments, the identifying feature unique to a quantification level and the hybridization domain may comprise the same nucleotide sequence (i.e., a single nucleotide sequence that can serve as both a unique identifying feature and that can stably hybridize with a target sequence under suitable reaction conditions).

As described above, blocking primers also comprise a hybridization domain capable of binding to a complementary sequence within the target. The hybridization domain of the blocking primers must at least partially correspond to the hybridization domain of the quantification primers so that the blocking primers and quantification primers compete for binding to the target. In other words, blocking primers must be able to bind or overlap the same region of the target as the quantification primers, or otherwise obstruct interaction of the quantification primers with the target, in order to interfere with the binding of the quantification primers. In some embodiments of the invention, the hybridization domains of the quantification primers and the blocking primers are identical. In some embodiments of the invention, the quantification primers and blocking primers are polynucleotides comprising hybridization domains that are at least 70%, 75%, 80%, 85%, 90%, 95%, 98% or 99% identical; i.e., have 0-3 base mismatches for every 10 nucleotide sequence. Furthermore, blocking primers are also generally bifunctional in the sense that they comprise an isolation feature (e.g., nucleotide sequence) in addition to a hybridization domain. As described above, the isolation feature or sequence facilitates removal of unbound blocking primers and blocking primer/target pairs. In some embodiments, the isolation feature is polynucleotide tail. In particular embodiments, the isolation feature is a polyA tail. In other embodiments, the isolation feature is any polynucleotide sequence other than a polyA tail that can bind to a complementary polynucleotide sequence affixed to a solid support. In such embodiments, the isolation sequence is at least 40%, at least 50%, at least 60%, at least 70% or more dissimilar to any portion of the quantification primers not intended to bind the target (e.g., the unique identifying sequence)

Embodiments of the invention further comprise anti-hybridization ("anti-hyb") primers that comprise a domain to facilitate removal of unbound quantification primers (and blocking primers). In some embodiments, the domain is a polynucleotide sequence that is substantially similar to at least part of the target area bound by the quantification and blocking primers; i.e., it is at least partially complementary to part of the hybridization domains of the quantification and blocking primers. Thus, anti-hyb primers can bind to the hybridization domains of the quantification and blocking primers as long as the quantification and blocking primers are not bound to a target. Furthermore, anti-hyb primers are also generally bifunctional in the sense that they comprise an isolation feature in addition to an anti-hybridization domain. As described above, the isolation feature facilitates removal of anti-hyb/unbound quantification primer pairs and anti-hyb/unbound blocking primer pairs by, for example, interaction with a complementary feature affixed to a solid support. In some embodiments, the isolation feature is polynucleotide tail. In particular embodiments, the isolation feature is a polyA tail. In other embodiments, the isolation feature is any polynucleotide sequence other than a polyA tail that can bind to a complementary polynucleotide sequence affixed to a solid support. In some embodiments of the invention, the isolation feature of the anti-hyb primers is different from the isolation feature of the blocking primers.

In some embodiments of the invention, the primers are polynucleotides. In such embodiments, the primers comprise a nucleotide sequence that is capable of hybridizing to a complementary sequence in the target, as discussed above. Hybridization can be conducted under suitable hybridization conditions, which may vary in stringency as desired. Stringency of hybridization may be controlled by both temperature and salt concentration. For example, the conditions of hybridization to achieve selective hybridization may involve hybridization in high ionic strength solution at a temperature that is approximately 12-25° C. below the Tm (the melting temperature at which half of the molecules dissociate from their hybridization partners). The temperature and salt conditions may be determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. *Methods Enzymol.* 1987:154:367, 1987). Stringency of hybridization can be reduced accordingly as the degree of complementarity desired is decreased, and further, depending upon the G-C or A-T richness of the primers. Likewise, stringency of hybridization can be increased accordingly as the desired level of homology is increased, and further, depending upon the G-C or A-T richness of any area wherein high homology is desired, all as known in the art. The duration of hybridization may be generally less than about one day, to less than about 12 hours, to less than about 4 hours, to less than about 1 hour, to approximately several minutes.

In some embodiments, polynucleotide primers may be approximately 100-90, 90-80, 80-70, 70-60, 60-50, 50-40, 40-30 or 30-20 base pairs in length. Polynucleotide primers may comprise a hybridization sequence or structure that is capable of binding to a complementary sequence or structure in a target. In some embodiments, this sequence or structure is between 10 and 100 nucleotides in length, or between about 12 and 50 nucleotides in length, and is capable of forming a hybrid with complementary sequence in the target such that it is sufficiently stable under stringent hybridization conditions. The hybrids may comprise RNA:RNA, RNA:DNA, or DNA:DNA duplex molecules or duplex molecules containing analogs of these nucleic acids. It will be appreciated that substantially corresponding primers of the invention can vary from strict complementarity and still hybridize. Variation from a canonical complementary nucleic acid may be stated in terms of a percentage of identical bases within the sequence or the percentage of perfectly complementary bases between the capture moiety and the tag. For example, in some embodiments, primers are substantially complementary and capable of hybridizing if they are 100% to 80% complementary to the target, or have 0-2 base mismatches in a 10 nucleotide sequence.

Primers of the present disclosure may be prepared by any of a variety of methods (see, e.g., Sambrook et al., "*Molecular Cloning: A Laboratory Manual*", 1989, $2^{nd}$ Ed., Cold Spring Harbour Laboratory Press: New York, N.Y.; "*PCR Protocols: A Guide to Methods and Applications*", 1990, Innis (Ed.), Academic Press: New York, N.Y.; Tijssen "*Hybridization with Nucleic Acid Probes—Laboratory Techniques in Biochemistry and Molecular Biology (Parts I* and II)", 1993, Elsevier Science; "*PCR Strategies*", 1995, Innis (Ed.), Academic Press: New York, N.Y.; and "*Short Protocols in Molecular Biology*", 2002, Ausubel (Ed.), 5$^{th}$ Ed., John Wiley & Sons: Secaucus, N.J.). Capture tags and capture moieties may be single- or double-stranded, and may be comprised of DNA, RNA, proteins, or any combination thereof.

Primers may be prepared by chemical techniques well-known in the art, including, e.g., chemical synthesis and polymerization based on a template as described, e.g., in Narang et al., *Meth. Enzymol.* 68:90-98 (1979); Brown et al., *Meth. Enzymol.* 68: 109-151 (1979); Belousov et al., *Nucleic Acids Res.* 25:3440-3444 (1997); Guschin et al., *Anal. Biochem.* 250:203-211 (1997); Blommers et al., *Biochemistry* 33:7886-7896 (1994); Frenkel et al., *Free Radic. Biol. Med.* 19:373-380 (1995); and U.S. Pat. No. 4,458,066.

In some embodiments, the primers are prepared such that they comprise a hybridization domain that is at least partially single stranded. The hybridization domain itself comprises a motif (i.e., nucleotide sequence) that corresponds with and is capable of binding (e.g., hybridizing) to a corresponding motif in a target. Methods of generating single stranded polynucleotides adaptable for use in the present invention are known in the art (see, e.g., U.S. Pat. No. 5,066,584; U.S. Pat. No. 5,518,900; and U.S. Pre-grant publication 2010/0331193).

In some embodiments, primers may be prepared using an automated, solid-phase procedure based on the phosphoramidite approach. In such methods, each nucleotide is individually added to the 5'-end of the growing oligonucleotide chain, which is attached at the 3'-end to a solid support. The added nucleotides are in the form of trivalent 3'-phosphoramidites that are protected from polymerization by a dimethoxytriyl (or DMT) group at the 5'-position. After base-induced phosphoramidite coupling, mild oxidation to give a pentavalent phosphotriester intermediate and DMT removal provides a new site for oligonucleotide elongation. The oligonucleotides are then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc. (Foster City, Calif.), DuPont (Wilmington, Del.) or Milligen (Bedford, Mass.). Alternatively, primers can be custom made and ordered from a variety of commercial sources well-known in the art, including, for example, the Midland Certified Reagent Company (Midland, Tex.), ExpressGen, Inc. (Chicago, Ill.), Operon Technologies, Inc. (Huntsville, Ala.), and many others.

Purification, where necessary or desirable, may be carried out by any of a variety of methods well known in the art. For example, purification of oligonucleotides is typically performed either by native acrylamide gel electrophoresis, by anion-exchange HPLC, e.g., see Pearson and Regnier, *J. Chrom.* 255:137-149 (1983) or by reverse phase HPLC, e.g., see McFarland and Borer, *Nucleic Acids Res.* 7:1067-1080 (1979).

The sequence of primers can be verified using any suitable sequencing method including, but not limited to, chemical degradation, e.g., see Maxam and Gilbert, *Methods of Enzymology*, 65:499-560 (1980), Sanger sequencing, NGS sequencing, matrix-assisted laser desorption ionization time-of-flight (MALDI-TOF) mass spectrometry, e.g., see Pieles et al., *Nucleic Acids Res.* 21:3191-3196 (1993), and mass spectrometry following a combination of alkaline phosphatase and exonuclease digestions, e.g., see Wu and Aboleneh, *Anal. Biochem.* 290:347-352 (2001).

The present disclosure encompasses modified versions of quantification primers and blocking primers that perform as equivalents in accordance with the methods of the present disclosure. These modifications may be accomplished using any of several means known in the art. Non-limiting examples of such modifications include methylation, "caps", substitution of one or more of the naturally occurring nucleotides with an analog (e.g., nucleotide isoform analogs, including, but not limited to iso-C and iso-G bases), and internucleotide modifications such as, for example, those with uncharged linkages (e.g., methyl phosphonates, phosphotriesters, phosphoroamidates, carbamates, etc.), or charged linkages (e.g., phosphorothioates, phosphorodithioates, etc.). Modified oligonucleotides may also be derivatized by formation of a methyl or ethyl phosphotriester or an alkyl phosphoramidate linkage. Furthermore, primers of the present disclosure may also be modified with a label.

Labeling of Primers

In some embodiments, quantification primers may be labeled with a detectable agent to facilitate real-time quantification of targets. The role of a detectable agent is to allow visualization and detection of target sequences to which the agents are attached. In some embodiments, the detectable agents are associated with particular quantification levels, thereby allowing quantification of the target sequences to which the agents are directly or indirectly (i.e., via a quantification primer) bound. Preferably, the detectable agent is selected such that it generates a signal that is measurable, discrete and can be correlated with a particular quantification level to which the signal has been assigned. In some embodiments, the intensity of the signal is related (e.g., proportional) to the amount of target present. In some embodiments, blocking primers are labeled with detectable agents.

The association between the oligonucleotide and the detectable agent can be covalent or non-covalent. Labeled primers can be prepared by incorporation of or conjugation to a detectable moiety. Labels can be attached directly to the nucleic acid sequence or indirectly (e.g., through a linker). Linkers or spacer arms of various lengths are known in the art and are commercially available, and can be selected to reduce steric hindrance, or to confer other useful or desired properties to the resulting labeled molecules, e.g., see Mansfield et al., *Mol. Cell Probes* 9:145-156 (1995).

Various methods for labeling nucleic acid molecules are known in the art. For a review of labeling protocols and label detection techniques, see, for example, Kricka, *Ann. Clin. Biochem.* 39:114-129 (2002); van Gijlswijk et al., *Expert Rev. Mol. Diagn.* 1:81-91 (2001); and Joos et al., *J. Biotechnol.* 35:135-153 (1994). Standard nucleic acid labeling methods include: incorporation of radioactive agents, direct attachments of fluorescent dyes (Smith et al., *Nucl. Acids Res.* 13:2399-2412 (1985)) or of enzymes (Connoly and Rider, *Nucl. Acids. Res.* 13:4485-4502 (1985)); chemical modifications of nucleic acid molecules making them detectable immunochemically or by other affinity reactions, e.g., see Broker et al., *Nucl. Acids Res.* 5:363-384 (1978); Bayer et al., *Methods of Biochem. Analysis* 26:1-45 (1980); Langer et al., *Proc. Natl. Acad. Sci. USA* 78:6633-6637 (1981); Richardson et al., *Nucl. Acids Res.* 11:6167-6184 (1983); Brigati et al., *Virol.* 126:32-50 (1983); Tchen et al., *Proc. Natl. Acad. Sci. USA* 81:3466-3470 (1984); Landegent et al., *Exp. Cell Res.* 15:61-72 (1984); and Hopman et al., *Exp. Cell Res.* 169:357-368 (1987); and enzyme-mediated labeling methods, such as random priming, nick translation, PCR and tailing with terminal transferase. For a review on enzymatic labeling, see, e.g., Temsamani and Agrawal, *Mol.*

Biotechnol. 5:223-232 (1996). More recently developed nucleic acid labeling systems include, but are not limited to: ULS (Universal Linkage System), which is based on the reaction of monoreactive cisplatin derivatives with the N7 position of guanine moieties in DNA (Heetebrij et al., *Cytogenet. Cell. Genet.* 87:47-52 (1999)), psoralen-biotin, which intercalates into nucleic acids and upon UV irradiation becomes covalently bonded to the nucleotide bases (Levenson et al., *Methods Enzymol.* 184:577-583 (1990); and Pfannschmidt et al., *Nucleic Acids Res.* 24:1702-1709 (1996)), photoreactive azido derivatives (Neves et al., *Bioconjugate Chem.* 11:51-55 (2000)), and DNA alkylating agents (Sebestyen et al., *Nat. Biotechnol.* 16: 568-576 (1998)).

It will be appreciated that any of a wide variety of detectable agents can be used in the practice of the present disclosure. Suitable detectable agents include, but are not limited to, various ligands, radionuclides (such as, for example, $^{32}P$, $^{35}S$, $^{3}H$, $^{14}C$, $^{125}I$, $^{131}I$, and the like); fluorescent dyes; chemiluminescent agents (such as, for example, acridinium esters, stabilized dioxetanes, and the like); spectrally resolvable inorganic fluorescent semiconductor nanocrystals (i.e., quantum dots), metal nanoparticles (e.g., gold, silver, copper and platinum) or nanoclusters; enzymes (such as, for example, those used in an ELISA, e.g., horseradish peroxidase, beta-galactosidase, luciferase, alkaline phosphatase); colorimetric labels (such as, for example, dyes, colloidal gold, and the like); magnetic labels (such as, for example, Dynabeads™); and biotin, dioxigenin or other haptens and proteins for which antisera or monoclonal antibodies are available.

Measurement of Primer Levels

As described above, embodiments of the invention require knowledge of the approximate amount (i.e., copy number) of quantification primers and blocking primers added at each step. Nucleic acid amounts in nanograms or micrograms can readily be converted to copy number as long as the length of the primer is known. For example, the average mass of an RNA nucleotide can be approximated as 340 Daltons (Da), the mass of a DNA nucleotide can be approximated as 330 Da and the mass of a basepair (bp) in double-stranded DNA can be approximated as 660 Da. This makes the formula weight of RNA nucleotides 340 g, the formula weight of DNA nucleotides 300 g and the formula weight of the bp's in double stranded DNA 660 g. Using these numbers, the formula weight of any single or double strand of nucleotides can be estimated by taking the product of the strand length (in bases or bp's) and the average formula weight of the type of nucleotide in the strand. Using Avogadro's number ($6.022 \times 10^{23}$ molecules/mole) the number of molecules of the template per gram can be calculated. Other methods of estimating primer copy numbers are known in the art.

Primer concentration can also be measured by ultraviolet (UV) light spectroscopy, providing a first quantification. Optionally, a second quantification step can be performed using a fluorimetry technique with a DNA-specific dye (e.g., PicoGreen). Fluormetric DNA quantification techniques are known in the art. See, for example, Barcellos et al., Am. J. Hum. Genet., 1997, 61:737-747; Germer et al., Genome Res., 2000, 10:258-266; Breen et al., 2000, Biotechniques, 2000, 28:464-470; and Plomin et al., Behav. Genet., 2002, 31:497-509. Each sample can then be diluted to an exact concentration (e.g., 100 copies).

Solid Supports

Embodiments of the invention utilize anti-isolation features attached to solid supports to remove target copies bound by blocking primers, unbound blocking primers and unbound quantification primers. A wide variety of solid supports may be used, and it is not intended that the invention be limited to the use of any particular type of solid support. In some embodiments, the anti-isolation features are polynucleotides sequences that correspond to an isolation feature present in the primers (quantification primers, blocking primers and/or anti-hyb primers). A wide variety of nucleic acid sequences may be bound to a solid support in order to facilitate isolation of the corresponding sequence in the bound blocking primers, unbound blocking primers and unbound quantification primers. Likewise, the manner in which anti-isolation features are directly or indirectly attached to the solid support should not be limiting in any way.

In some embodiments embodiment, the anti-isolation features can be synthesized on the surface in a manner suitable for deprotection but not cleavage from the synthesis support (see, e.g., Weiler et al., *Nucl. Acids Res.*, 25(14): 2792-2799 (1997)). In still another embodiment, one or more anti-isolation features can be covalently linked to a surface by the reaction of a suitable functional group on the isolation features with a functional group of the surface (see, e.g., Geiger et al., *Nucleosides & Nucleotides* 17(9-11): 1717-1724 (1998)).

Methods for the chemical attachment of anti-isolation features to solid support surfaces can involve the reaction of a nucleophilic group, (e.g., an amine or thiol) of the anti-isolation features to be immobilized, with an electrophilic group on the solid support surface. Alternatively, the nucleophile can be present on the support and the electrophile (e.g., activated carboxylic acid) can be present on the anti-isolation features. In some embodiments, anti-isolation features may be attached to a solid support by click chemistry. In some embodiments, anti-isolation features are attached via a 1,3-cycloaddition of an azide with an alkyne, optionally in the presence of a copper catalyst. Methods of using click chemistry are known in the art and include those described by Rostovtsev et al., *Angew. Chem. Int. Ed.* 2002, 41: 2596-99 and Sun et al., *Bioconjugate Chem.,* 2006, 17: 52-57.

In some embodiments of the invention, anti-isolation features are directly attached to solid substrates via standard N-ethyl-N'-(dimethylaminopropyl)carbodiimide/N-hydroxysuccinimide (EDC/NHS) amine coupling procedures Amine coupling introduces N-hydroxysuccinimide esters into the surface matrix by modification of the carboxymethyl groups with a mixture of N-hydroxysuccinimide (NHS) and N-ethyl-N'-(dimethylaminopropyl)-carbodiimide (EDC). These esters then react spontaneously with amines and other nucleophilic groups on the capture moiety to form covalent links. This is a highly stable and common surface functionalization technique.

Numerous types of solid supports derivatized with amino groups, carboxylic acid groups, isocyantes, isothiocyanates and malimide groups are commercially available. Non-limiting examples of suitable solid supports include chips of any type (e.g., arrays), membranes, glass, controlled pore glass, polystyrene particles (beads), magnetic beads, capillary tubes, silica and gold nanoparticles. In some embodiments, the solid supports may be open wells or closed flowcells, wherein the solution comprising the targets is at least partially constrained by a solid substrate. In other embodiments, the solid supports may be functionalized particles, wherein the solid substrate is surrounded by a target-comprising solution. Small particles have the advantage of providing high surface area for binding coupled with ease of use in embodiments comprising centrifugation or magnetic separation.

Enzymatic Manipulations

As discussed above, in some embodiments of the invention, quantifying information may be incorporated or embedded into the targets so that it can be carried through until sequencing of the targets, at which time the unique identifying feature sequence can be determined and correlated to a quantification level assigned to that unique identifying sequence. In some embodiments, quantifying information is embedded by cDNA preparation following binding of quantification primers to single-stranded RNA targets.

When a cDNA preparation step is included in the disclosed methods, the method of cDNA preparation can be any method of cDNA preparation that produces enzymatically manipulatable cDNA. For example, the cDNA can be prepared by using, for example, random primers, poly-d(T) oligos, or NVd(T) oligos. Many examples exist of performing reverse transcription to produce cDNA for use in PCR, including the following: Glisin et al., *Biochemistry* 13:2633-7 (1974); Ullrich et al., *Science* 196:1313 (1977); Chirgwin et al., *Biochemistry* 18:5294-9 (1979); Faulkner-Jones et al., *Endocrinol.* 133:2962-2972 (1993); and Gonda et al., *Mol. Cell Biol.* 2:617-624 (1982). In some embodiments, quantification primers function to initiate cDNA synthesis.

Reverse transcriptases from any source (native or recombinant) may be used in embodiments of the present invention. Suitable reverse transcriptases include, but are not limited to, those from Moloney murine leukemia virus (M-MLV), human T-cell leukemia virus type I (HTLV-I), bovine leukemia virus (BLV), Avian Sarcoma Leukemia Viruses (ASLV) including Rous Sarcoma Virus (RSV) and Avian Myeloblastosis Virus (AMV), human immunodeficiency virus (HIV), cauliflower mosaic virus, *Saccharomyces, Neurospora, Drosophila*, primates, and rodents. See, for example, U.S. Pat. Nos. 4,663,290 and 6,063,60; Grandgenett et al., *Proc. Nat. Acad. Sci. (USA)* 70:230-234 (1973), Gerard, *DNA* 5:271-279 (1986), Kotewicz et al., *Gene* 35:249-258 (1985), Tanese et al., *Proc. Natl. Acad. Sci. (USA)* 82:4944-4948 (1985), Roth et al., *J. Biol. Chem.* 260:9326-9335 (1985), Michel et al., *Nature* 316:641-643 (1985), Akins et al., *Cell* 47:505-516 (1986) and *EMBO J.* 4:1267-75 (1985), and Fawcett, *Cell* 47:1007-1015 (1986); Shinnick et al., *Nature* 293:543-548 (1981); Seiki et al., *Proc. Natl. Acad. Sci. USA* 80:3618-3622 (1983); Rice et al., *Virology* 142:357-77 (1985); Schwartz et al., *Cell* 32:853-869 (1983); Larder et al., *EMBO J.* 6:3133-3137 (1987); Farmerie et al., *Science* 236:305-308 (1987); Barr et al., *Biotechnology* 5:486-489 (1987)); Tanese et al., *J. Virol.* 59:743-745 (1986); Hansen et al., *J. Biol. Chem.* 262:12393-12396 (1987); Sonigo et al., *Cell* 45:375-85 (1986); Takatsuji et al., *Nature* 319:240-243 (1986); Toh et al., *Nature* 305:827-829 (1983)); Alexander et al., *J. Virol.* 61:534-542 (1987); and Yuki et al., *Nucl. Acids Res.* 14:3017-3030 (1986). High fidelity reverse transcriptases are preferred. Reverse transcriptases without nuclease activity are also preferred.

In some embodiment, PCR amplification may be used to embed quantifying information into targets. Additionally or alternatively, PCR amplification can be used to amplify targets after reverse transcription or to otherwise increase the amount of target for sequencing after quantifying information has been embedded so that original input target levels can be determined. The basis of nucleic acid amplification are well-known in the art (see, for example, Kimmel and Berger, *Methods Enzymol.* 152: 307-316 (1987); Sambrook et al., "*Molecular Cloning: A Laboratory Manual*", 1989, $2^{nd}$ Ed., Cold Spring Harbor Laboratory Press: New York, N.Y.; "*Short Protocols in Molecular Biology*", Ausubel (Ed.), 2002, $5^{th}$ Ed., John Wiley & Sons: Secaucus, N.J.).

Such nucleic acid amplification methods include, but are not limited to, the Polymerase Chain Reaction (or PCR, described, for example, in "*PCR Protocols: A Guide to Methods and Applications*", Innis (Ed.), 1990, Academic Press: New York; "*PCR Strategies*", Innis (Ed.), 1995, Academic Press: New York; "*Polymerase chain reaction: basic principles and automation in PCR: A Practical Approach*", McPherson et al. (Eds.), 1991, IRL Press: Oxford; Saiki et al., *Nature* 324:163 (1986); and U.S. Pat. Nos. 4,683,195, 4,683,202 and 4,889,818); reverse transcriptase polymerase chain reaction (or RT-PCR, described in, for example, U.S. Pat. Nos. 5,322,770 and 5,310,652); emulsion PCR (Dressman et al., *Proc. Natl. Acad. Sci. USA,* 2003, 100:8817-8822); and solid-phase amplification (Fedurco et al., *Nucleic Acids Res.,* 2006, 34:e22).

The PCR (or polymerase chain reaction) technique is well-known in the art. In its simplest form, PCR is an in vitro method for the enzymatic synthesis of specific DNA sequences, using two primers that hybridize to opposite strands and flank the region of interest in the target DNA. In some embodiments, one of those primers is a quantification primer. In some embodiments, one of the primers is a "reverse primer" (or "Rev primer"). Reverse primers are non-tailed (i.e., no polyA tail or other isolation feature) primers that enable PCR amplification and are located at the opposite end of the region of interest to be amplified. (FIG. 3). A plurality of reaction cycles, each cycle comprising: a denaturation step, an annealing step, and a polymerization step, results in the exponential accumulation of a specific DNA fragment, including the unique identifying sequences of the quantification primers; see for example, "*PCR Protocols: A Guide to Methods and Applications*", Innis (Ed.), 1990, Academic Press: New York; "*PCR Strategies*", Innis (Ed.), 1995, Academic Press: New York; "*Polymerase chain reaction: basic principles and automation in PCR: A Practical Approach*", McPherson et al. (Eds.), 1991, IRL Press: Oxford; Saiki et al., *Nature* 324:163-166 (1986). The termini of the amplified fragments are defined as the 5' ends of the primers. Examples of DNA polymerases capable of producing amplification products in PCR reactions include, but are not limited to: *E. coli* DNA polymerase I, Klenow fragment of DNA polymerase I, T4 DNA polymerase, thermostable DNA polymerases isolated from *Thermus aquaticus* (Taq) which are available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). High fidelity polymerases are preferred. Polymerase without nuclease activity are also preferred. RNA target sequences may be amplified by reverse transcribing the mRNA into cDNA, and then performing PCR (RT-PCR), as described above. Alternatively, a single enzyme may be used for both steps as described in U.S. Pat. No. 5,322,770.

The duration and temperature of each step of a PCR cycle, as well as the number of cycles, are generally adjusted according to the stringency requirements in effect. Annealing temperature and timing are determined both by the efficiency with which a primer is expected to anneal to a template and the degree of mismatch that is to be tolerated. The ability to optimize the reaction cycle conditions is well within the knowledge of one of ordinary skill in the art.

Although the number of reaction cycles may vary depending on the detection analysis being performed, it usually is at least 15, more usually at least 20, and may be as high as 60 or higher. However, in many situations, the number of reaction cycles may range from about 20 to about 40.

The denaturation step of a PCR cycle generally comprises heating the reaction mixture to an elevated temperature and maintaining the mixture at the elevated temperature for a period of time sufficient for any double-stranded or hybridized nucleic acid present in the reaction mixture to dissociate. For denaturation, the temperature of the reaction mixture is usually raised to, and maintained at, a temperature ranging from about 85° C. to about 100° C., usually from about 90° C. to about 98° C., and more usually about 90° C. to about 94° C. for a period of time ranging from about 3 to about 120 seconds, usually from about 5 to about 30 seconds. In some embodiments, the first cycle is preceded by an elongated denaturation step ranging from about 1 to 10 minutes, usually from about 2 to 5 minutes.

Following denaturation, the reaction mixture is subjected to conditions sufficient for primer annealing to template DNA present in the mixture. The temperature to which the reaction mixture is lowered to achieve these conditions is usually chosen to provide optimal efficiency and specificity, and generally ranges from about 45° C. to about 75° C., usually from about 50° C. to about 70° C., and more usually from about 53° C. to about 55° C. Annealing conditions are generally maintained for a period of time ranging from about 15 seconds to about 30 minutes, usually from about 30 seconds to about 1 minute.

Following annealing of primer to template DNA or during annealing of primer to template DNA, the reaction mixture is subjected to conditions sufficient to provide for polymerization of nucleotides to the primer's end in a such manner that the primer is extended in a 5' to 3' direction using the DNA to which it is hybridized as a template (i.e., conditions sufficient for enzymatic production of primer extension product). To achieve primer extension conditions, the temperature of the reaction mixture is typically raised to a temperature ranging from about 65° C. to about 75° C., usually from about 67° C. to about 73° C., and maintained at that temperature for a period of time ranging from about 15 seconds to about 20 minutes, usually from about 30 seconds to about 5 minutes. In some embodiments, the final extension step is followed by an elongated extension step ranging from ranging from about 1 to 10 minutes, usually from about 2 to 5 minutes.

The above cycles of denaturation, annealing, and polymerization may be performed using an automated device typically known as a thermal cycler or thermocycler. Thermal cyclers that may be employed are described in U.S. Pat. Nos. 5,612,473; 5,602,756; 5,538,871; and 5,475,610. Thermal cyclers are commercially available, for example, from Perkin Elmer-Applied Biosystems (Norwalk, Conn.), Bio-Rad (Hercules, Calif.), Roche Applied Science (Indianapolis, Ind.), and Stratagene (La Jolla, Calif.).

In some embodiments, one or both of the PCR reactions are "kinetic PCR" (kPCR) or "kinetic RT-PCR" (kRT-PCR), which are also referred to as "real-time PCR" and "real-time RT-PCR," respectively. These methods involve detecting PCR products via a probe that provides a signal (typically a fluorescent signal) that is related to the amount of amplified product in the sample. These methods can be utilized in embodiments of the invention where quantification information is embedded into quantification primers via attachment of a detectable agent (e.g., probe or beacon) that is specific for a particular quantification level. Examples of commonly used detectable agents in kPCR and kRT-PCR include those used in the following probes: TAQMAN® probes, Molecular Beacons probes, SCORPION® probes, and SYBR® Green probes. Briefly, TAQMAN® probes, Molecular Beacons, and SCORPION® probes each have a fluorescent reporter dye (also called a "fluor") attached to the 5' end of the probes and a quencher moiety coupled to the 3'end of the probes. In the unhybridized state, the proximity of the fluor and the quench molecules prevents the detection of fluorescent signal from the probe. During PCR, when the polymerase replicates a template on which a probe is bound, the 5'-nuclease activity of the polymerase cleaves the probe thus, increasing fluorescence with each replication cycle. In some embodiments of the invention, each quantification level can be associated with a different and specific fluorescence. SYBR® Green probes binds double-stranded DNA and upon excitation emit light; thus as PCR product accumulates, fluorescence increases.

In some embodiments, the PCR reaction is used in a "single-plex" PCR assay. "Single-plex" refers to a single assay that is not carried out simultaneously with any other assays. Single-plex assays include individual assays that are carried out sequentially.

In some embodiments, the PCR reaction is used in a "multiplex" PCR assay. The term "multiplex" refers to multiple assays that are carried out simultaneously, in which detection and analysis steps are generally performed in parallel. Targets from different samples can be multiplexed at any point after quantification information is embedded (so that original input levels can be determined in a sample-specific manner) in order to increase throughput. Mutliplexing requires a means of correlating a target with its original sample; such means have been described previously (see U.S. provisional application 61/672,833, filed Jul. 18, 2012, and references disclosed therein, incorporated by reference herein in their entirety.].

In some embodiments, a first amplification step amplifies a region of a target gene. In some embodiments the amplification product is less than about 1500, 1400, 1300, 1200, 1100, 1000, 900, 800, 700, 600, 500, 400, 300, 250, 225, 200, 175 or 150 nucleotides long.

Sequencing

Nucleic acid sequencing, in its broadest sense, comprises determination of the identity of a nucleotide at a given position within an oligonucleotide or polynucleotide. Sequencing of nucleic acids, such as deoxyribonucleic acid (DNA) and ribonucleic acid (RNA), involves determining the order of the nucleotide bases, namely adenine, guanine, cytosine, uracil, and thymine contained within a genetic sample (e.g., DNA from a blood sample). In some embodiments, sequencing comprises detecting the differences of at least one nucleotide between two nucleic acids. Examples of techniques for detecting differences of at least one nucleotide between two nucleic acids include, but are not limited to, selective oligonucleotide hybridization, selective amplification, or selective primer extension. For example, oligonucleotide probes may be prepared in which the known polymorphic nucleotide is placed centrally and then hybridized to target DNA under conditions which permit hybridization only if a perfect match is found, e.g., see Saiki et al., *Nature* 324:163 (1986); Saiki et al., *Proc. Natl Acad. Sci USA* 86:6230 (1989); and Wallace et al., *Nucl. Acids Res.* 6:3543 (1979). Such specific oligonucleotide hybridization techniques may be used for the simultaneous detection of several nucleotide changes in different polymorphic regions of DNA. For example, oligonucleotides having nucleotide sequences of specific allelic variants are attached to a hybridizing membrane and this membrane is then hybridized with labeled sample nucleic acid. Analysis of the hybridization signal will then reveal the identity of the nucleotides of the sample nucleic acid. Alternatively unlabeled sample nucleic acid may be immobilized and contacted with labeled oligonucleotides that hybridize selectively with specific allelic variants.

Real-time pyrophosphate DNA sequencing is yet another approach to determine nucleotide sequence identity; see, for example, Alderborn et al., *Genome Research*, 10(8):1249-1258 (2000). Additional methods include, for example, PCR amplification in combination with denaturing high performance liquid chromatography (dHPLC); see, for example, Underhill et al., *Genome Research*, 7(10):996-1005 (1997).

In some embodiments, any of a variety of sequencing reactions known in the art can be used to directly sequence at least a portion of the target. In some embodiments, any of a variety of sequencing reactions known in the art can be used to directly sequence at least a portion of amplified DNA and detect tropic variants. The sequence can be compared with the sequences of known tropic variants to determine which one(s) are present in the sample. Exemplary sequencing reactions include those based on techniques developed by Maxam and Gilbert, *Proc. Natl. Acad. Sci USA*, 74:560 (1977) or Sanger, *Proc. Nat. Acad. Sci* 74:5463 (1977). It is also contemplated that any of a variety of automated sequencing procedures may be utilized when performing the subject assays, e.g., see Venter et al., *Science*, 291:1304-1351 (2001); Lander et al., *Nature*, 409:860-921 (2001), including sequencing by mass spectrometry, e.g., see U.S. Pat. No. 5,547,835 and PCT Patent Publication No. WO 94/16101 and WO 94/21822; U.S. Pat. No. 5,605,798 and PCT Patent Application No. PCT/US96/03651; Cohen et al., *Adv. Chromatogr.* 36:127-162 (1996); and Griffin et al., *Appl. Biochem. Biotechnol.* 38:147-159 (1993). It will be evident to one skilled in the art that, for some embodiments, the occurrence of only one, two or three of the nucleic acid bases need be determined in the sequencing reaction. Yet other sequencing methods are disclosed, e.g., in U.S. Pat. Nos. 5,580,732; 5,571,676; 4,863,849; 5,302,509; PCT Patent Application Nos. WO 91/06678 and WO 93/21340; Canard et al., *Gene* 148:1-6 (1994); Metzker et al., *Nucleic Acids Research* 22:4259-4267 (1994) and U.S. Pat. Nos. 5,740,341 and 6,306,597.

In some embodiments, following the enzymatic manipulation describe above to embed the quantification information into the targets, traditional Sanger sequencing can be used to generate a set of fragments with a common 5' origin and base-specific 3' termini. The 3' termini are created by base-specific interruption of in vitro enzymatic synthesis by the incorporation of chain-terminating nucleotide analogs. Targets to be sequenced are typically cloned into a vector (e.g., bacteriophage M13) that allows the fragment to be isolated as single-stranded DNA, although similar methods can be applied for double-stranded DNA. However procured, isolated single-stranded DNA serves as a template for DNA polymerase-catalyzed reactions. The template is primed by an oligonucleotide primer complementary to a known or engineered sequence 3' to the sequence of interest. DNA polymerase extends the primer to copy the sequence of interest. In embodiments disclosed herein, the oligonucleotide primer must be situated so that the unique identifying sequence is copied. The polymerase reactions take place in the presence of deoxyribonucleoside triphosphate analogs, 2',3'-dideoxyribonucleoside triphosphates (ddNTPs), which terminate chain extension because they lack 3' hydroxyl termini.

A series of fragments terminated in a particular base is generated by running the DNA polymerase reaction in the presence of equivalent concentrations of the four deoxyribonucleotide triphosphates (e.g., dCTP, dGTP, dTTP), plus a one-tenth concentration of one of the nucleotides in dideoxy form. Thus, the DNA polymerase will occasionally insert the dideoxy nucleotide adjacent to its complementary base in the target. This stops chain elongation, which results in the fragment being released from the polymerase. A series of double-stranded fragments of varying lengths is generated, with the newly synthesized strand of each fragment terminating in the selected dideoxynucleotide (e.g., ddATP), which identifies the complementary base (e.g., T) in the sequence of interest. Sites terminating in the other bases are identified by running comparable polymerase reactions with the other three dideoxy analogs. Traditionally, a radioactive label is included in the polymerization mixture. Thus, gel electrophoresis followed by radioautography can be used to generate four sequencing ladders, with each ladder specific to a particular base.

Variations of Sanger sequencing have been developed that allow for automated sequence determination. A red, blue, green or yellow fluorescent dye is attached to the 5' end of the sequencing primers. Each of the four sequencing reactions is run with a different color primer, thereby assigning characteristic fluorescence to all the fragments terminating in a particular base. Eliminating the use of radioisotopes favors high-throughput applications as the use of fluorescent dyes allows for automated determination of the sequence reads and processing of the data.

In modern automated Sanger sequencing systems, the sequence is determined by high-resolution electrophoretic separation of the end-labeled extension products in a capillary-based polymer gel. Laser excitation of the fluorescent labels as fragments of discrete lengths exit the capillaries, in combination with four-color detection of emission spectra, provide the sequencing trace. Software translates these traces into DNA sequence and generates error probabilities for each base-call. Applications of the Sanger system can now be applied to achieve read-lengths of approximately 1000 base pairs and accuracies above 99.9%.

Automated Sanger sequencing is referred to as a "first generation" technology. Preferred embodiments of the invention utilize "next-generation sequencing" ("NGS") technologies, which can cheaply provide enormous volumes of sequence data (e.g., in excess of one billion short reads per sequencing runs). NGS technologies may be applied to a broad range of biological phenomena, including genetic variation, RNA expression, protein-DNA interactions, evolutionary comparisons, and chromosome conformation analyses.

Next generation sequencing (NGS), as used herein, refers to array-based sequencing protocols utilizing cycles of enzymatic manipulation and imaging-based data collection. Widely used NGS platforms include 454 sequencing, Illumina/Solexa technology, the SOLiD platform, the Polonator, and the HeliScope Single Molecule Sequencer Technology. In most platforms, genomic or other target DNA is randomly fragmented and ligated in vitro to common adaptor sequences to form templates that are attached or immobilized (directly or indirectly) to a solid support Immobilization of spatially separated template sites allows thousands to billions of sequencing reactions to be performed simultaneously. In certain NGS platforms, templates are clonally amplified by emulsion PCR, bridge PCR (see, e.g., Adessi et al., *Nucleic Acids Res.*, 2000, 28:e87; Fedurco et al., *Nucleic Acids Res.*, 2006, 34:e22) or in situ polonyzation (Mitra and Church, *Nucleic Acids Res.*, 1999, 27:e34). Other NGS platforms (e.g., HeliScope) utilize single-molecule templates, i.e., a single molecule is spatially separated and immobilized (e.g., bound by a primer attached to solid support) on a solid support and subject to enzymatic manipulation without the need for amplification. NGS platforms also differ in the type of enzymatic manipulation that is applied. Several widely used platforms rely on "sequencing-by-synthesis", in which a DNA polymerase serially extends a primed and bound template by incorporation of fluorescently labeled nucleotides. Enzymatic manipulation in some platforms is achieved via a ligase, in which a fluorescently labeled probe hybridizes to its complementary sequence adjacent a primed template and DNA ligase is added to join the dye-labeled probe to the primer. NGS platforms for use in embodiments of the invention have been described previously. See, for example, Metzker, M. L., *Nature Review Genetics*, 2010, 11:31-46; Shendure J. and Hanlee, J., *Nat. Biotech.*, 2008, 26:1135-1145.

Multiplexed DNA sequencing can also be used in embodiments of the invention. Methods of multiplexed DNA sequencing to which embodiments of the present invention may be adapted have been described previously; see, for example, U.S. Pat. No. 6,480,791 and U.S. pre-grant publication 2010/0113283. Those of skill in the art will appreciate that multiplexing imparts a significant advantage to embodiments of the present invention. Multiplex samples and/or targets may be handled in parallel, which allows all subsequent processing and analysis (e.g., sequencing) to be conducted in parallel. For example, multiplexing significantly increases the rate of DNA sequencing reactions, e.g., from hundreds to thousands of bases per hour. In embodiments of the invention, the number of samples that can be multiplexed for parallel analysis may range from 5-10, 10-100, 100-500 or more.

It will be appreciated that a target need not necessarily be amplified prior to sequencing. Single molecule templates can be prepared for sequencing reactions. See, for example, Harris et al., *Science*, 2008, 320:106-109. For example, quantification primers can be designed to incorporate an isolation sequence comprising 3-10 amino acids. This isolation sequence may, but need not, be separate from the identifying sequence, but should be single-stranded when bound to the target and separate from the hybridization domain. Spatially distributed individual primer molecules with sequences complementary to the single-stranded isolation sequence may be covalently attached to a solid support. Following application of the quantification protocols described above the quantification primers and the targets to which they're bound can be hybridized to the immobilized primers. A DNA polymerase is added to bind to the immobilized primed template configuration to initiate an NGS sequencing reaction. Furthermore, certain NGS protocols (e.g., nanopore sequencing) may be able read sequences without amplification. Thus, after isolation and purification of the quantification primer/target hybrids, it may be possible to denature the quantification probe and sequence it directly to obtain the quantifying information.

Kits

In some embodiments, the present disclosure provides kits comprising materials useful for the quantification and genotyping (sequencing) of biological targets according to methods described herein. The inventive kits may be used by diagnostic laboratories, experimental laboratories, or practitioners.

Materials and reagents useful for the quantification and genotyping of biological targets according to the present disclosure may be assembled together in a kit. (see, e.g., FIG. 2). In some embodiments, an inventive kit comprises groups of quantification primers pre-assigned to particular quantification levels with hybridization domains specific to one or more targets. An inventive kit further comprises blocking primers comprising hybridization domains that are identical or substantially identical to the hybridization domain of the quantification primers and an isolation feature (e.g., nucleotide sequence) to facilitate its isolation via, for example, attachment to a solid support. An inventive kit further comprises anti-hyb primers for isolation of unbound quantification primers, comprising a domain identical or substantially identical to the hybridization target region and an isolation feature to facilitate isolation (e.g., a polyA tail). An inventive kit optionally comprises a solid support to which anti-isolation features have been bound (e.g., magnetic poly-dT beads) and reverse primers for PCR amplification. In some embodiment, a kit may also comprise reveres transcription and/or amplification reaction reagents for PCR amplification. In some embodiments, a kit comprises reagents and components which render the procedure specific. Thus, a kit may be intended to be used for quantification and sequencing of a particular subset of targets (e.g., the V3 loop of the HIV-1 viral envelope protein).

Suitable reverse transcription/amplification reaction reagents that can be included in an inventive kit include, for example, one or more of: buffers; enzymes having reverse transcriptase and/or polymerase activity; enzyme cofactors such as magnesium or manganese; salts; nicotinamide adenine dinuclease (NAD); and deoxynucleoside triphosphates (dNTPs) such as, for example, deoxyadenosine triphosphate; deoxyguanosine triphosphate, deoxycytidine triphosphate and deoxythymidine triphosphate, biotinylated dNTPs, suitable for carrying out the amplification reactions.

Depending on the procedure, the kit may further comprise one or more of: wash buffers and/or reagents, hybridization buffers and/or reagents, labeling buffers and/or reagents, and detection means. The buffers and/or reagents included in a kit are preferably optimized for the particular amplification/detection technique for which the kit is intended. Protocols for using these buffers and reagents for performing different steps of the procedure may also be included in the kit.

Furthermore, the kits may be provided with an internal control as a check on the amplification procedure and to prevent occurrence of false negative test results due to failures in the amplification procedure. An optimal control sequence is selected in such a way that it will not compete with the target nucleic acid sequence in the amplification reaction (as described above).

Kits may also contain reagents for the isolation of nucleic acids from biological specimens prior to amplification and/or for nucleic acid extraction or the purification or separation of the same.

The reagents may be supplied in a solid (e.g., lyophilized) or liquid form. The kits of the present disclosure optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the amplification/detection assay may also be provided. The individual containers of the kit are preferably maintained in close confinement for commercial sale.

The kit may also comprise instructions for using the kit according to one or more methods of the present disclosure, e.g., instructions for processing the biological sample, extracting nucleic acid molecules, and/or performing the test; instructions for interpreting the results as well as a notice in the form prescribed by a governmental agency (e.g., FDA) regulating the manufacture, use or sale of pharmaceuticals or biological products.

In certain embodiments, the kits of the invention are adaptable to high-throughput and/or automated operation. For example, the kits may be suitable for performing assays in multi-well plates and may utilize automated fluid handling and/or robotic systems, plate readers, etc.

Embodiments of the invention are further defined by reference to the following examples.

EXAMPLES

Example 1

Synthesis of Bifunctional Quantification Primers

In accordance with embodiments described above, quantification primers are synthesized by techniques well known to those of skill in the art. In this particular example, quantification primers are chemically synthesized. The primers are designed to comprise two domains: (1) a target-specific hybridization domain; and (2) a unique identifying sequence assigned to a first quantification level (e.g., 1000 level or 10,000 level). It will be appreciated by those of skill in the art that the two domains can be located on separate areas of the primers, can be adjacent to one another, can partially overlap, and can even be designed such that they completely overlap.

The third hypervariable domain ("V3") of the gp120 envelope glycoprotein of HIV-1 is a critical determinant of its tropism. Thus, primers are designed with oligonucleotide sequences for determining HIV coreceptor tropism (CCR5 or CXCR4) by amplifying the V3 region of the HIV env genomic sequence. Two such hybridization domains are:

(SEQ ID NO: 1)
EMF1: AGA GAA AGA GCA GAA GAC AGT GGC;

(SEQ ID NO: 2)
EMR1: CCT TGT AAG TCA TTG GTC TTA AAG GTA CC.

These oligonucleotides are provided as primer sets to amplify an V3 region of the HIV env gene, e.g., to determine which polymorphic variant(s) is/are present among some or all of the possible polymorphic variants that may exist at a particular polymorphic site. Primer Set 1 comprises a forward primer comprising SEQ ID NO: 1, or any active fragment thereof, and a reverse primer comprising SEQ ID NO: 2, or any active fragment thereof. Those of skill in the art will appreciate that the exact length of hybridization domains may vary according to the particular target sequence and PCR parameters, and can be any length acceptable for PCR.

Seven primer sets are then synthesized such that a unique identifying sequence assigned to a particular quantification level is included 5' to the hybridization domain of the forward primer. The exemplary seven unique index sequences are:

TABLE 1

| Index Sequence | Index Name | Quantification level |
|---|---|---|
| ATCACG | A001 | $10^2$ |
| CGATGT | A002 | $10^3$ |

TABLE 1-continued

| Index Sequence | Index Name | Quantification level |
|---|---|---|
| TTAGGC | A003 | $10^4$ |
| TGACCA | A004 | $10^5$ |
| ACAGTG | A005 | $10^6$ |
| GCCAAT | A006 | $10^7$ |
| CAGATC | A007 | $10^8$ |

It will be readily apparent to those of skill in the art that the index sequences do not necessarily have to be limited to six nucleotides. Index sequences may consist of as few as three nucleotides, and may be at least 50 nucleotides. It will also be readily apparent that any index sequence can be assigned to any quantification level, as long as the index sequence is unique and specific for that level (i.e., is not duplicated in a quantification primer corresponding to another quantification level). An example of a complete quantification primer set specific to the EMF1 target is as follows:

TABLE 2

| Quantification Level | Sequence (5' to 3') |
|---|---|
| 102 | *ATCACG* AGA GAA AGA GCA GAA GAC AGT GGC (SEQ ID NO: 3) |
| 103 | *CGATGT* AGA GAA AGA GCA GAA GAC AGT GGC (SEQ ID NO: 4) |
| 104 | *TTAGGC* AGA GAA AGA GCA GAA GAC AGT GGC (SEQ ID NO: 5) |
| 105 | *TGACCA* AGA GAA AGA GCA GAA GAC AGT GGC (SEQ ID NO: 6) |
| 106 | *ACAGTG* AGA GAA AGA GCA GAA GAC AGT GGC (SEQ ID NO: 7) |
| 107 | *GCCAAT* AGA GAA AGA GCA GAA GAC AGT GGC (SEQ ID NO: 8) |
| 108 | *CAGATC* AGA GAA AGA GCA GAA GAC AGT GGC (SEQ ID NO: 9) |

A suitable sequence located at the opposite end of the region to be amplified is chosen for the reverse primer. For example, EMR1 described above serves as the paired primer for EMF1 to amplify across an appropriate region of envelope gene.

Example 2

Synthesis of Blocking and dA-antiHyb Primers

Blocking primers are synthesized as above such that they comprise the same target-specific hybridization domain as the quantification primer. The blocking primers further comprise an isolation sequence. In this example, the isolation sequence is a polyA tail. In general, when the isolation sequence is a polyA tail, it can be 5' or 3' and can be approximately 10 to 50 nucleotides in length. An exemplary blocking primer for the EMF1 target is: AAAAAAAAAAAAAAAAAAAA AGA GAA AGA GCA GAA GAC AGT GGC (SEQ ID NO: 10).

dA-antiHyb primers are also synthesized as above, which are used to remove free quantification primers not bound to targets. Such primers are synthesized such that they contain a sequence corresponding to the quantification-target-binding region and a polyA tail for ease of isolation. An example of a dA-antiHyb primer for the EMF1 target is: AAAAAAAAAAAAAAAAAAAA TCT CTT TCT CGT CTT CTG TCA CCG (SEQ ID NO: 11).

Example 3

Quantification

A validation assay is designed to test the quantification of 300,000 copies of an RNA target comprising the sequence of the gp120 envelope glycoprotein of HIV-1. The following parameters are chosen for the validation assay: 100 quantification primers per labeling step, up to $10^8$ dynamic range and a logarithmic scale granularity in factors of 10.

A 1 ml target solution comprising approximately 300,000 single-stranded copies of the target is prepared by measurement and dilution of a sample obtained from a HIV positive subject. HIV-1 RNA is extracted from plasma samples by means of a commercially available kit according to manufacturer's instructions. The target solution also comprises a number of negative control sequences (i.e., not comprising the sequence of the gp120 envelope glycoprotein) in order to validate the specificity of the primers.

Figure 4:
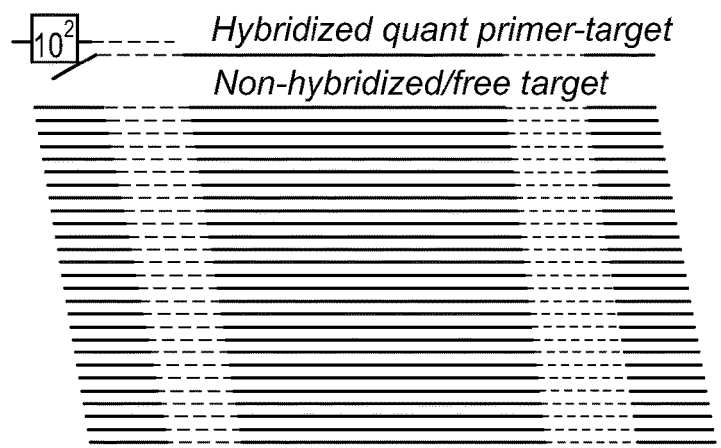
FIGS. 4-14 illustrate an exemplary embodiment of the invention, including cycles of steps of quantification and blocking (FIGS. 4-9), isolation of blocked targets, unbound blocking primers and unbound quantification primers (FIGS. 10 and 11), reverse transcription to embed quantifying information into target copies (FIG. 12), optional PCR amplification (FIG. 13), and DNA sequencing (FIG. 14).
Figure 5:
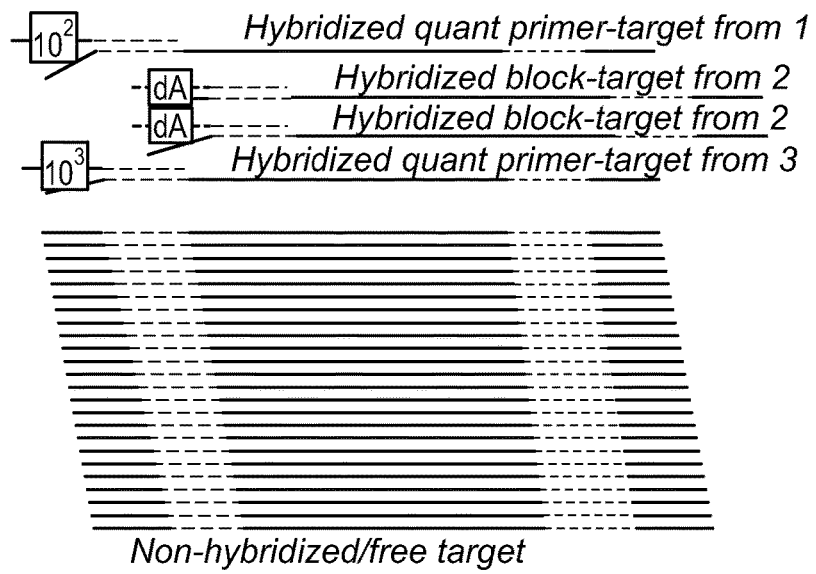
Figure 6:
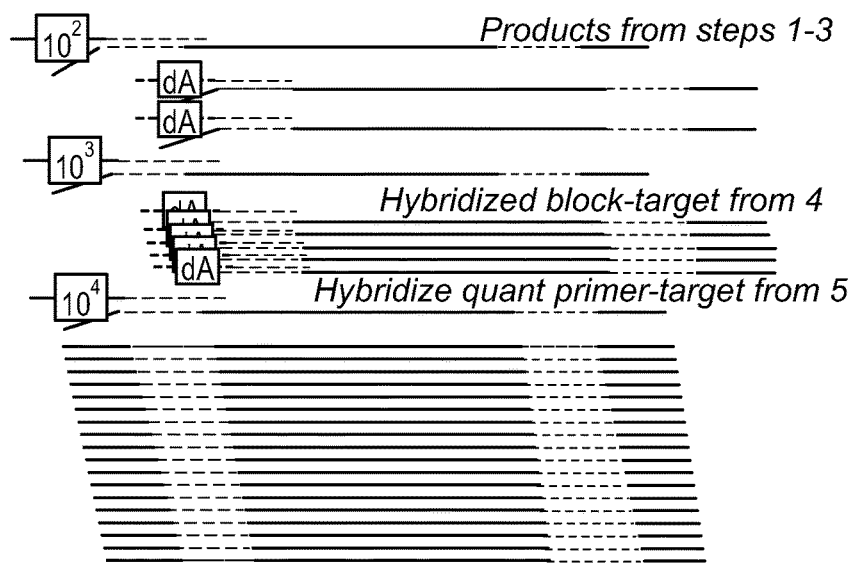
Figure 7:
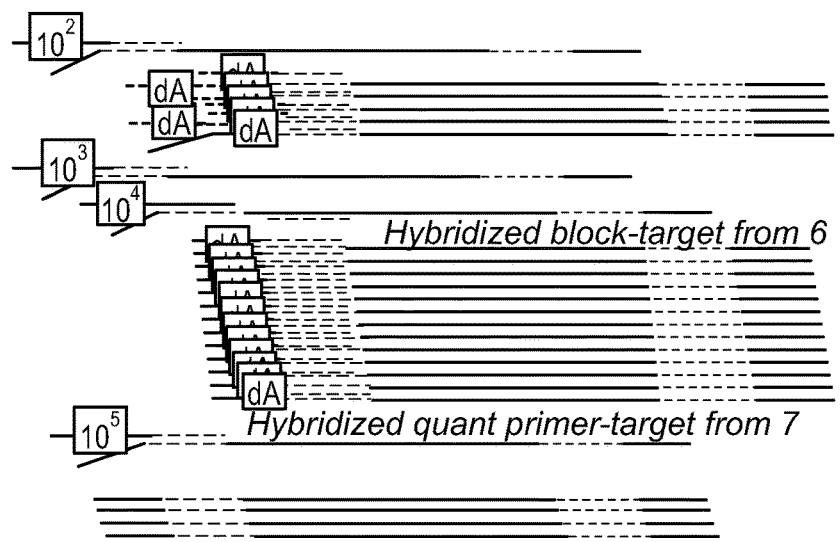
Figure 8:
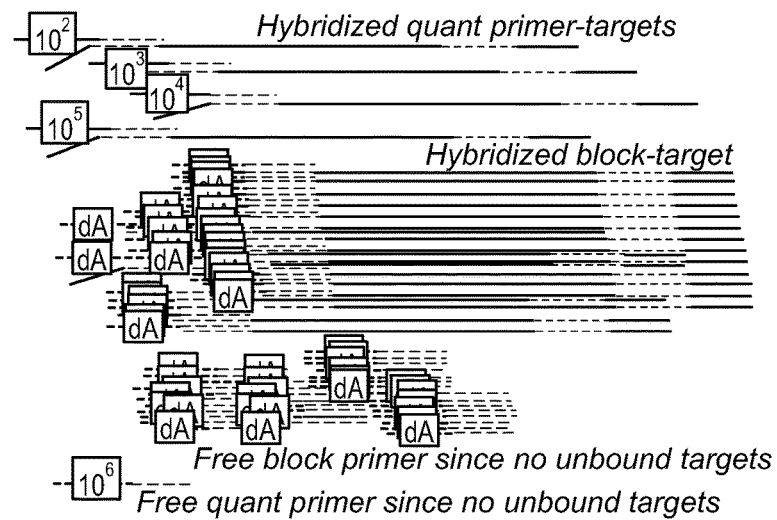
Figure 9:
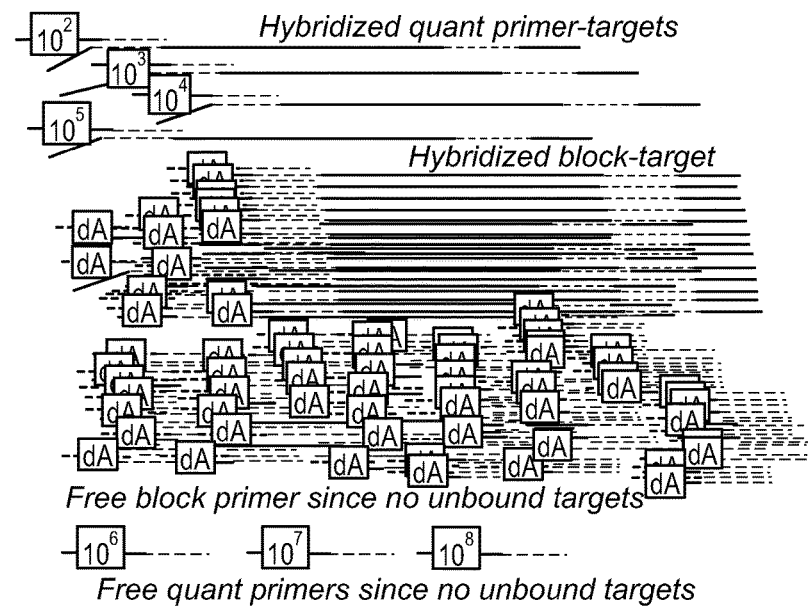

100 copies of the quantification primer assigned to the "$10^2$" quantification level (i.e., comprising the ATCACG identification feature; (SEQ ID NO: 3)) are added to the solution and allowed to bind for minutes to hours. (FIG. 4). After the appropriate amount of time has elapsed, 1000 copies of the blocking primer (SEQ ID NO: 10) are added to the solution and allowed to hybridize to free target not bound by the "$10^2$" quantification primer. (FIG. 5). After a reasonable amount of time has elapsed, 100 copies of the quantification primer assigned to the "$10^3$" quantification level (SEQ ID NO: 4) are added to the solution and allowed to bind to free target as in the preceding step. Next, $10^4$ copies of the blocking primer are added to the solution and allowed to hybridize to free target. (FIG. 6). This step is followed by addition of 100 copies of the quantification primer assigned to the "$10^4$" quantification level (SEQ ID NO: 5). Next, $10^5$ copies of the blocking primer are added, followed by addition of 100 copies of the quantification primer assigned to the "$10^5$" quantification level (SEQ ID NO: 6). (FIG. 7). After an appropriate amount of time has elapsed to allow the "$10^5$" quantification primers to hybridized to any free target, $10^6$ copies of the blocking primer are added to the solution. (FIG. 8). After the blocking primer is given time to hybridized, 100 copies of the quantification primer assigned to the "$10^6$" quantification level (SEQ ID NO: 7) are added the solution. In the next step, $10^7$ copies of the blocking primer are added to the solution and allowed to hybridize to any free copies of the target. This is followed by addition of 100 copies of the quantification primer assigned to the "$10^7$" quantification level (SEQ ID NO: 8). In the final step, $10^8$ copies of the blocking primers are added and, after an appropriate amount of time has elapsed to allow the blocking primers to hybridize to free copies of the target, 100 copies of the quantification primer assigned to the "$10^8$" quantification level (SEQ ID NO: 9) are added. (FIG. 9).

Figure 10:
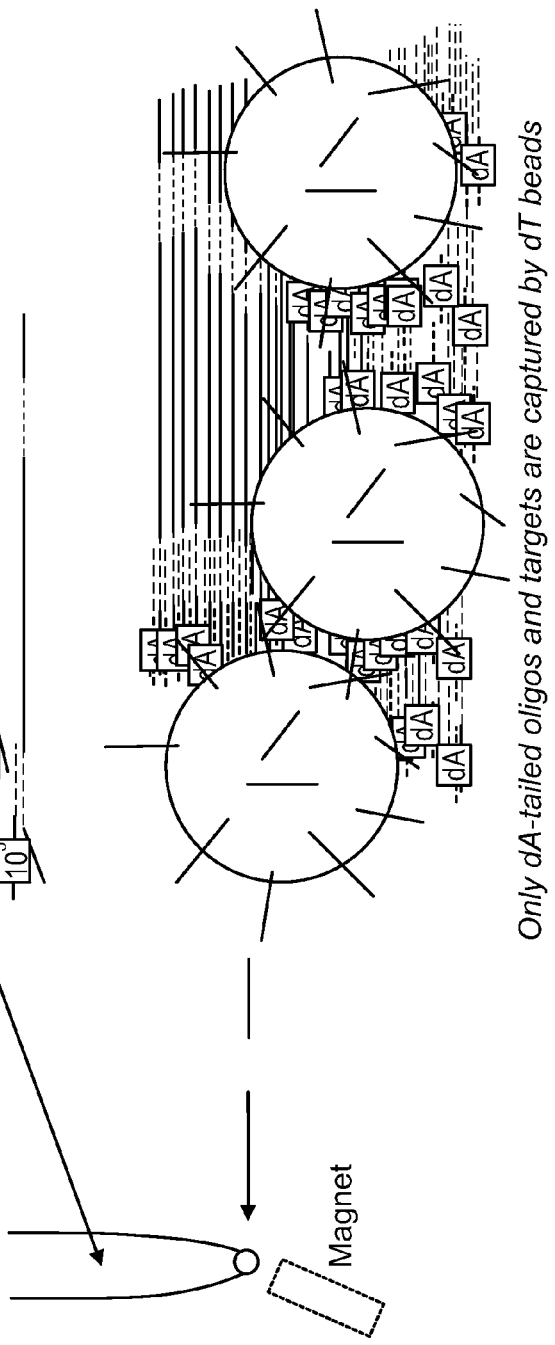
Figure 11:
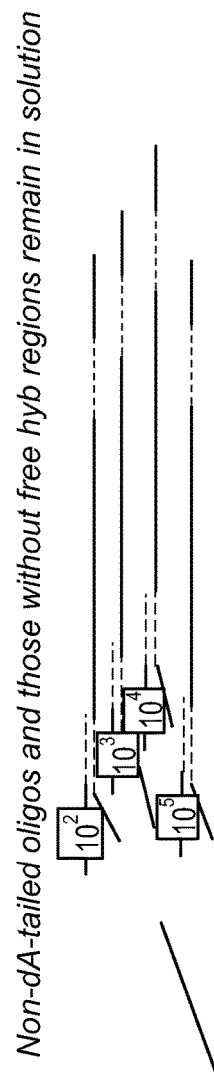
Figure 11:
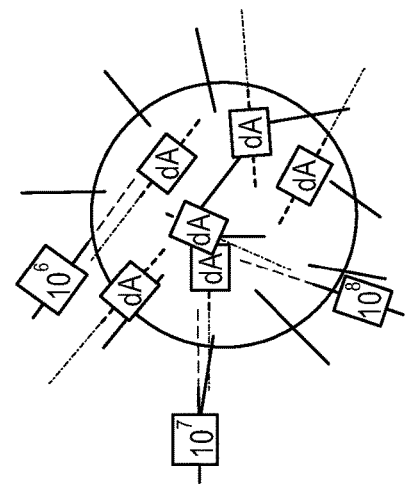

After all of the quantification primers and blocking primers have been added, magnetic oligo dT beads are added to the solution and mixed by agitation. The mixture is kept at well below melting temperature for a reasonable amount of time to allow the oligo dT sequences of the magnetic beads to interact/hybridize with polyA sequences present in the blocking primers. The beads, which bind to the blocking primers whether unbound or hybridized to the target, are then pulled-down by applying a magnet to the bottom of the tube. (FIG. 10). The subsequent solution, which comprises unbound quantification primers (which lack an oligo dT isolation feature) and targets bound by the quantification primers, is isolated and transferred to a second tube.

dA-antiHyb primers (SEQ ID NO: 11) comprising a sequence complementary to the hybridization domain of the quantification primers, are added, at 10-100× excess over the quantification primers, to the solution in the second tube. The tube is mixed by agitation and kept well below melting temperature for a reasonable amount of time to allow interaction with the hybridization domain of any unbound quantification primers. Oligo dT magnetic beads are again added to the solution and mixed by agitation, thereby allowing the beads to interact and binding the polyA sequences present in the dA-antiHyb primers. Thus, any residual dA-tailed oligonucleotides and dA-antiHyb oligos are bound by the beads and can be removed from the solution by applying a magnet. (FIG. 11).

Figure 12:
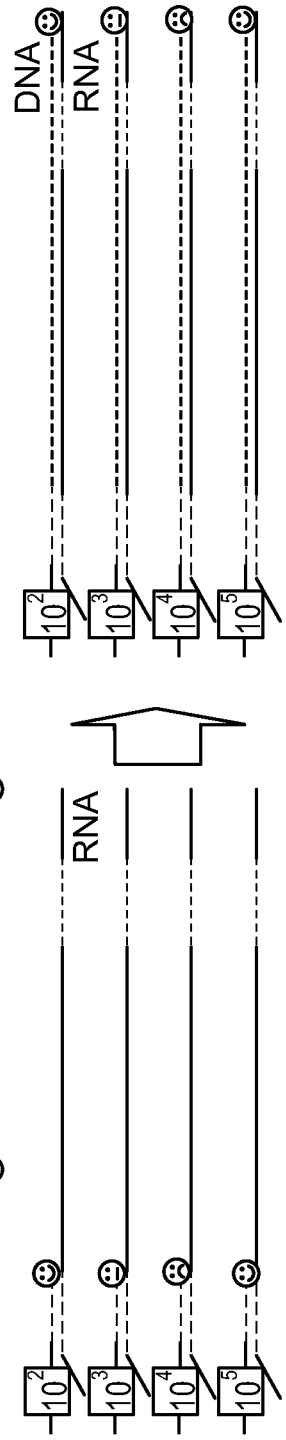
Figure 13:
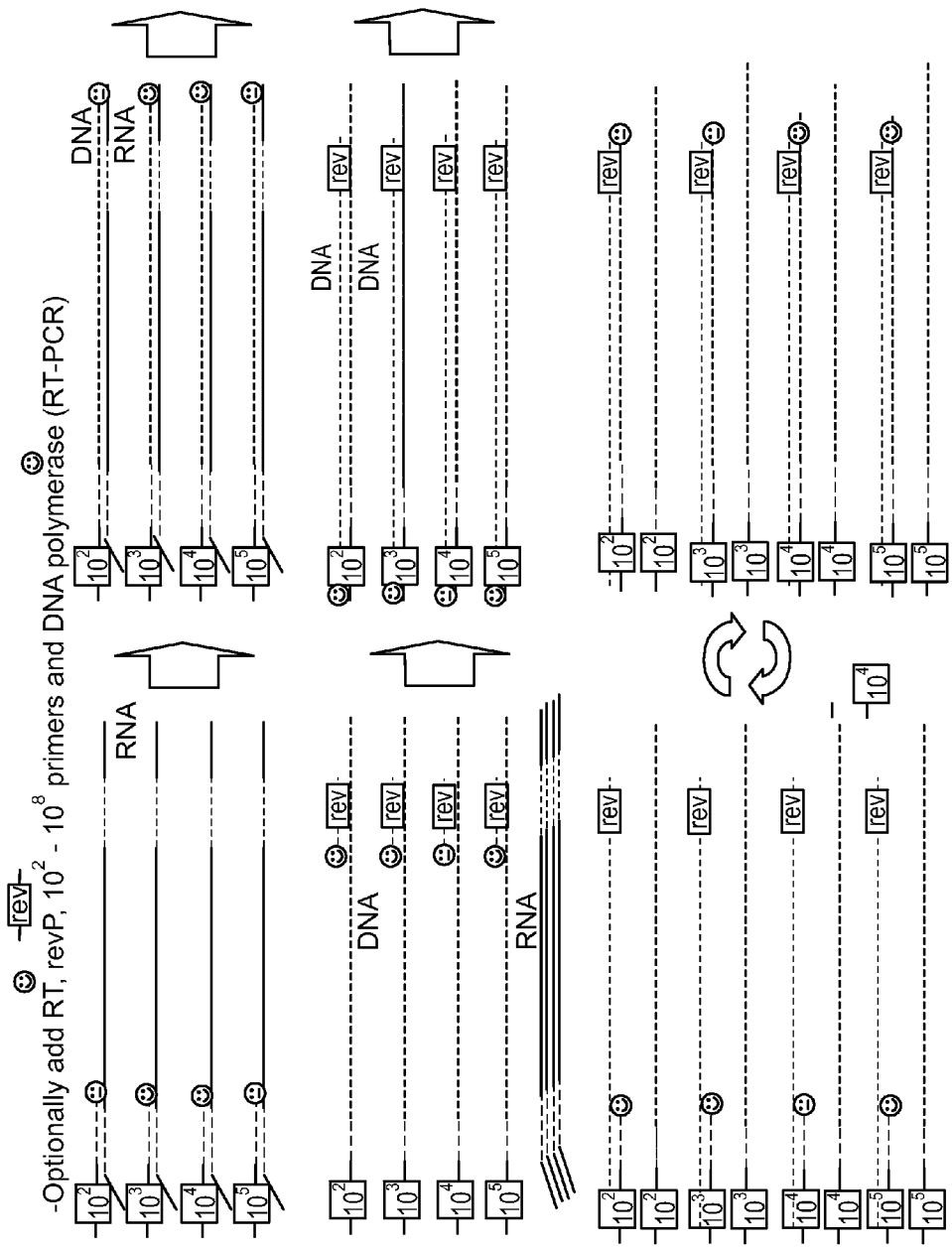

The target-bound quantification primers provide an exposed 3' hydroxyl group to prime reverse transcription of the isolated RNA targets. (FIG. 12). Following reverse transcription, the target copies can be readily amplified via PCR by inclusion of a complementary reverse primer (SEQ ID NO: 2) and thermostable DNA polymerase (i.e. rt-PCR). (FIG. 13). Conditions for reverse transcription and amplification of V3-containing regions of the env gene are known in the art (see, e.g., Svicher, V. et al., *New Microbiologica*, 2010, 33: 195-206.) Reverse transcription and/or amplification utilizing the quantification primers serves to encapsulate the quantification information present within the primers into the reaction products. Those of skill in the art will appreciate that amplification is a necessary precursor for accurate sequencing of low copy number targets, although certain embodiments of the invention do not require amplification.

Example 4

Sequencing

Figure 14:
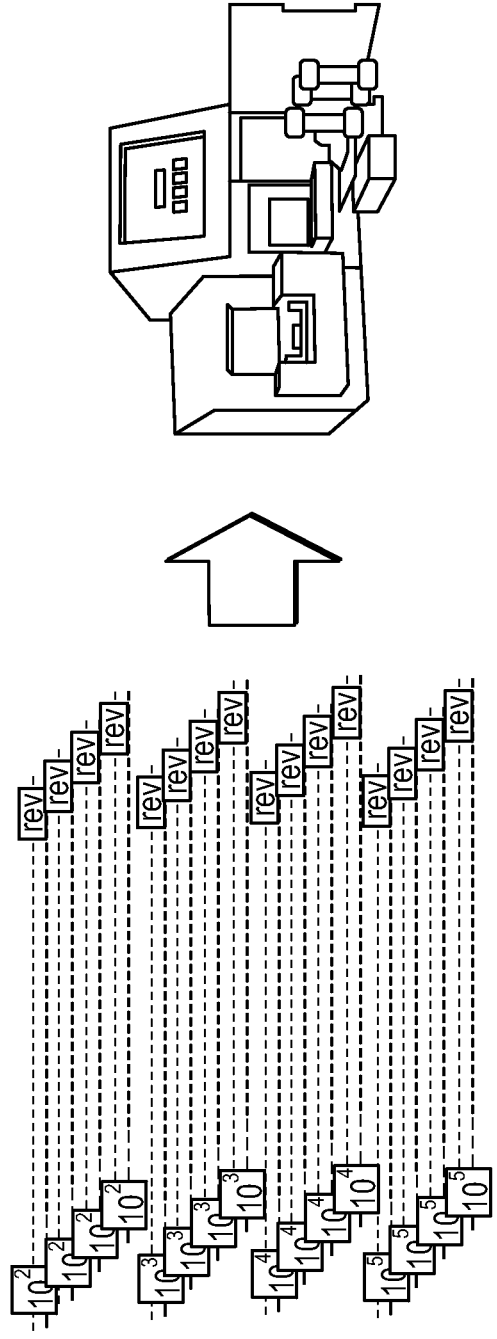

The amplified targets described above are sequenced via next-generation sequencing techniques as described in Metzker, M. L., *Nature Review Genetics*, 2010, 11:31-46, and Shendure J. and Hanlee, J., *Nat. Biotech.*, 2008, 26:1135-1145. (FIG. 14). Sequencing reveals the genotype (e.g., tropism) of the target and also provides a read-out of the unique identifying sequence (i.e. barcodes) corresponding to the quantification levels described and assigned in Example 1. The following identifying sequences are identified:

TABLE 3

| Index Sequence | Index Name | Quantification level |
|---|---|---|
| ATCACG | A001 | $10^2$ |
| CGATGT | A002 | $10^3$ |
| TTAGGC | A003 | $10^4$ |
| TGACCA | A004 | $10^5$ |

Notably, the presence of Index A004 (TGACCA), corresponding to a quantification of "$10^5$", indicates that there are at least 100,000 copies of the target. In other words, the addition of the 100 copies of the quantification primer assigned to the "$10^5$" quantification level (SEQ ID NO: 6) succeeded in hybridizing to the last remaining free copies of the target. Moreover, the absence of any index sequence corresponding to a quantification level of "$10^6$" or above indicates that fewer than 1,000,000 copies of the targets are present. By the point at which the "$10^6$" quantification primers are added to the solution in Example 3, there are no unbound targets to which the "$10^6$" quantification primers can hybridize and be subsequently encapsulated into the target after amplification. Thus, for a validation assay with a controlled target number (300,000), the sequencing-based quantification described herein provides an appropriately accurate approximation of the target number. It will be appreciated by those of skill in the art that the granularity (i.e., numerical spacing) between the quantification levels can be reduced (i.e., increased resolution) to provide a more accurate approximation by decreasing the amount of blocking primers added per step. This will, of course, increase the number of steps required to reach a given dynamic reach (i.e., the maximal desired detectable quantify).

Equivalents

Those skilled in the art will recognize, or be able to ascertain using no more than routine experimentation, many equivalents to the specific embodiments of the inventions described herein. The scope of the present disclosure is not intended to be limited to the scope of the above description, but rather is as set forth in the following claims.

All references cited herein are incorporated by reference in their entirety.

What is claimed is:

1. A method of quantitating the amount of a target nucleic acid in a sample, the method comprising:
   (1) obtaining a sample including a target nucleic acid;
   (2) contacting the sample with a quantification primer, wherein the quantification primer
      (a) comprises a hybridization domain complementary to a region of the target, and
      (b) comprises a unique identifying feature assigned to a first quantification level;
   (3) adding a quantity of blocking primer to the sample, wherein the blocking primer
      (a) is present in the same amount or in excess of the amount of quantification primer,
      (b) can bind at least a part of the region of the target that is complementary to the quantification primer, thereby blocking the region from contact with the quantification primer, and
      (c) binds a portion of the amount of the target in the sample not bound by quantification primer, wherein said portion is less than or equal to the quantity of blocking primer;
   (4) repeating steps (2) and (3) until the total quantity of blocking primer present in the sample meets or exceeds the amount of target present in the sample, wherein each repetition utilizes a quantification primer comprising a different unique identifying feature assigned to sequentially increasing quantification levels, and wherein the quantity of blocking primer added at each repetition establishes numerical spacing between the quantification levels; and
   (5) identifying the unique identifying feature present in any bound quantification primers that remain in the sample;
   wherein the presence of a unique identifying feature assigned to a particular quantification level indicates the approximate amount of the target present in the sample.

2. The method of claim 1, further comprising transcribing or amplifying targets bound by quantification primers into templates, thereby incorporating the unique identifying features into the templates.

3. The method of claim 2, further comprising sequencing at least a portion of a template.

4. The method of claim 3, wherein at least the unique identifying feature present in the template is sequenced.

5. The method of claim 1, wherein the unique identifying feature is a nucleotide sequence.

6. The method of claim 3, wherein substantially all of the template is sequenced.

7. The method of claim 1, wherein the numerical spacing is a log scale.

8. The method of claim 1, wherein the numerical spacing increases linearly by a factor of at least 100 between consecutive quantification levels.

9. The method of claim 1, wherein the numerical spacing increases linearly by a factor of approximately 1000 between consecutive quantification levels.

10. The method of claim 1, wherein one or more steps are automated.

11. The method of claim 1, wherein the target nucleic acid is viral RNA.

12. The method of claim 1, wherein the blocking primer further comprises an isolation feature that facilitates removal of unbound blocking primer and target bound by the blocking primer from the sample.

13. The method of claim 12, wherein the blocking primer isolation feature is a nucleotide sequence.

14. The method of claim 13, wherein unbound blocking primer and targets bound by the blocking primer are removed from the sample by hybridization of the isolation sequence with a solid substrate.

15. The method of claim 14, wherein the solid substrate is an antibody, magnetic bead, particle, polymeric bead, chromatographic resin, filter paper, membrane or hydrogel.

16. The method of claim 13, wherein the isolation sequence is a poly-adenosine tract.

17. The method of claim 15, wherein the solid substrate is a magnetic bead comprising oligonucleotides with a poly-thymine sequence.

18. The method of claim 1, further including removing any target bound by blocking primers, unbound blocking primers and unbound quantification primers from the sample, wherein removing unbound quantification primers from the sample comprises adding to the sample an anti-hybridization primer comprising (1) a sequence complementary to the hybridization domain of the quantification primer and (2) an isolation sequence.

19. The method of claim 18, wherein the isolation sequence is a poly-adenosine tract.

20. The method of claim 18, further comprising adding to the sample a solid substrate comprising a sequence complementary to the isolation sequence and removing the solid substrate once hybridized to unbound quantification primers.

21. The method of claim 20, wherein the solid substrate is an antibody, magnetic bead, particle, polymeric bead, chromatographic resin, filter paper, membrane or hydrogel.

22. The method of claim 21, wherein the solid substrate is a magnetic bead comprising oligonucleotides with a poly thymidine sequence.

23. The method of claim 5, wherein sequencing at least the unique identifying sequence present in the template indicates the presence of a polymorphism present in the target nucleic acid.

24. The method of claim 1, wherein the same amount of blocking primer is added at each repetition.

25. The method of claim 1, wherein the quantification primers in each repetition are identical except for the unique identifying sequence.

26. The method of claim 1, wherein, initially or during at least one repetition, the quantification primer is present in an amount less than the amount of target present in the sample.

27. The method of claim 1, wherein, initially or during at least one repetition, the quantification primer is present in an amount equal to the amount of target present in the sample.

28. The method of claim 1, wherein, initially or during at least one repetition, the quantification primer is present in an amount exceeding the amount of target present in the sample.

* * * * *